United States Patent [19]

Takahashi et al.

[11] Patent Number: 5,658,923
[45] Date of Patent: Aug. 19, 1997

[54] AZEPINE DERIVATIVES AND USE THEREOF

[75] Inventors: Nobuyuki Takahashi; Daisuke Mochizuki, both of Tagata-gun, Japan

[73] Assignee: Asahi Kasei Kogyo Kabushiki Kaisha, Osaka, Japan

[21] Appl. No.: 413,285

[22] Filed: Mar. 30, 1995

Related U.S. Application Data

[63] Continuation of PCT/JP95/00264, Feb. 23, 1995, which is a continuation-in-part of Ser. No. 389,385, Feb. 16, 1995, abandoned.

[30] Foreign Application Priority Data

Sep. 18, 1992 [JP] Japan .................. 4-250158
Oct. 6, 1992 [JP] Japan .................. 4-267702
Mar. 17, 1994 [JP] Japan .................. 6-047012

[51] Int. Cl.⁶ .......................... C07D 221/24; A61K 31/44
[52] U.S. Cl. ................................. 514/299; 546/112
[58] Field of Search ..................... 546/112; 514/299

[56] References Cited

U.S. PATENT DOCUMENTS

| | | | |
|---|---|---|---|
| 3,328,390 | 6/1967 | Grogan | 540/585 |
| 3,408,446 | 10/1968 | Keck | 514/323 |
| 5,187,277 | 2/1993 | Komissarov et al. | 544/362 |

FOREIGN PATENT DOCUMENTS

| | | |
|---|---|---|
| 23 41 925 A1 | 3/1975 | Germany . |
| 29 14 052 A1 | 10/1979 | Germany . |
| 852971 | 11/1960 | United Kingdom . |
| 1053085 | 12/1966 | United Kingdom . |

OTHER PUBLICATIONS

Keld Hermansen, "A New Series of Central Depressants: N-Alkylaryl Camphidines", Acta pharmacol. et toxicol., 1960, 17, 277-287.

Kurt Rubinstein, Keld Hermansen and Niels Elming, "N-Substituted 3-Azabicyclo [3.2.1] octanes", Acta Chemica Scandinavica, 1963, 17, 2069-2078.

Charles H. Grogan and Leonard M. Rice, "ω-Azabicyclic Butyrophenones", J. Medicinal Chemistry, 1967, 10, 621-623.

Torizo Takahashi, Hajime Fujimura, and Yoshio Hamashima, "Syntheses of Analygesics. XXXV. Camphane Derivatives. (6). Syntheses of Camphorimide and its Derivatives", Yakagaku Zasshi, 1964, 84 (10), 918-929. Pertinent portions in English also provided.

Grant R. Krow and Steven Szczepanski, "Unusual Regiochemistry in a Beckmann–Like Rearrangement of Camphor, α–Camphidone via Methylene Migration", Tetrahedron Letters, 1980, 21, 4593-4596.

N. Satyanarayana, H. R. Shitole and U. R. Nayak, "Camphor/Longicamphor & 7β–Formylnorlongifolane/ 7β–Acetylnorlongifolane Oximes: A Comparative Beckmann Rearrangement Study", Indian Journal of Chemistry, 1985, 24B, 997-1001.

J. Keck, G. Kruger, K. Noll and H. Machleidt, "Synthesen von neuen Amino–Halogen–substituierten Phenyl–aminoathanolen", Arzneim.–Forsch. (Drug Res.) 1972, 22(5), 861-869.

Eckard Weber, Mark Sonders, Merrit Quarum, Stafford McLean, Sovitj Pou, and John F. W. Keana, "1,3-Di(2-[5-3H]tolyl)guanidine: A selective ligand that labels σ-type receptors for psychotomimetic opiates and antipsychotic drugs", Proc. Natl. Acad. Sci. USA, 1986, 83, 8784-8788.

Primary Examiner—Philip I. Datlow
Attorney, Agent, or Firm—Pennie & Edmonds LLP

[57] ABSTRACT

An azepine compound of the formula

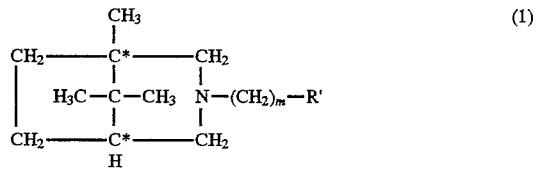

(1)

wherein R is (a)

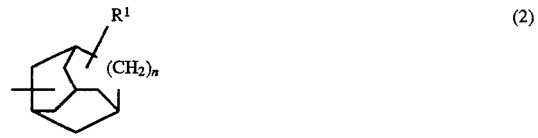

(2)

in which $R^1$ is hydrogen, lower alkyl, lower alkoxy, hydroxy, halogen, or optionally substituted phenyl, and n is 0 or 1, (b) cycloalkyl of $C_{5-8}$ which is optionally substituted by lower alkyl, (c) norbornyl, (d) bicyclo[3.3.1]nonyl, (e) naphthyl, (f) 1,3-benzoxolyl, (g) pyridyl, or (h) thienyl, m is an integer of 0-4, and C* is an asymmetric carbon, and nontoxic salts thereof, processes for producing the same, and therapeutic agents containing the same as the active ingredient for treating diseases related to σ-receptor. The compound (1) and nontoxic salts thereof have a high affinity for σ-receptor but scarcely any affinity for other receptors, thus being utilized for treating diseases related to σ-receptor, such as schizophrenia.

17 Claims, 1 Drawing Sheet

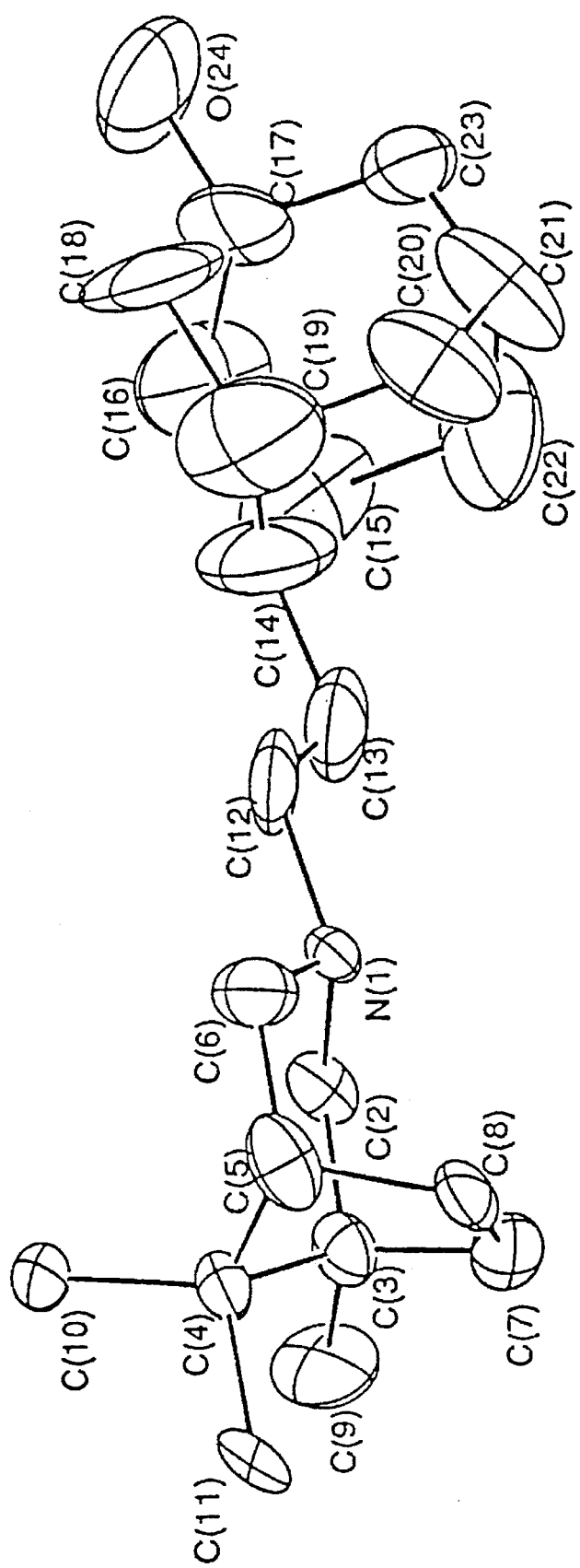
F I G. 1

AZEPINE DERIVATIVES AND USE THEREOF

This application is a continuation of PCT/JP95/00264, filed Feb. 23, 1995, continuation-in-part of Ser. No. 08/389,385 filed Feb. 16, 1995, now abandoned.

FIELD OF THE INVENTION

The present invention relates to azepine derivatives having activity for specific binding to σ-receptors, to the production thereof, to intermediates useful in the production thereof, and to pharmaceutical uses thereof.

BACKGROUND OF THE INVENTION

A σ-receptor has been defined as one of the opioid receptor including with μ-, δ-, κ- and ε-receptor. At present, the σ-receptor is classified not as opiate but as an independent receptor because an opioid antagonist naloxon has no affinity to a σ-receptor.

Pharmacological action through σ-receptor has not been investigated. Psychotomimetic drug phencyclidine has affinities for σ-receptor other than NMDA receptor, and antipsychotic drug haloperidol has been known to bind strongly σ-receptor other than dopamine receptor. Therefore, σ-receptor may participate psychic function, however no specific drug for σ-receptor has been reported.

British Patent 852971 (1959), Acta pharmacol. et Toxicol., 17, 277–287 (1960) and Acta Chemica Scandinavica, 17, 2069–2078 (1963) disclosed N-substituted phenylalkyl camphidine derivative of the formula $$
\begin{array}{c}
\text{CH}_3 \\
\text{CH}_2\text{---}\text{C}\text{---}\text{CH}_2 \\
| \quad \quad | \\
\text{H}_3\text{C}\text{---}\text{C}\text{---}\text{CH}_3 \quad \text{N}\text{---}(\text{CH}_2)_m\text{---}\bigcirc\text{R}_1\text{R}_2\text{R}_3\text{R}_4 \\
| \quad \quad | \\
\text{CH}_2\text{---}\text{C}\text{---}\text{CH}_2 \\
\text{H}
\end{array}
$$

wherein $R_1$, $R_2$, $R_3$ and $R_4$ are H, Cl, —$NO_2$, —$NH_2$, —$CH_3$, —$OCH_3$ or —OH and m is an integer of 1–3, and indicated the usefulness for depressor activity upon the central nervous system and tranquilizer.

Yakugaku Zasshi, 84(10), 918–929 (1964) disclosed N-substituted phenylalkyl camphidine derivative of the formula $$
\begin{array}{c}
\text{CH}_3 \\
\text{CH}_2\text{---}\text{C}\text{---}\text{CH}_2 \\
| \quad \quad | \\
\text{H}_3\text{C}\text{---}\text{C}\text{---}\text{CH}_3 \quad \text{N}\text{---}(\text{CH}_2)_m\text{---}\bigcirc\text{---}\text{R}' \\
| \quad \quad | \\
\text{CH}_2\text{---}\text{C}\text{---}\text{CH}_2 \\
\text{H}
\end{array}
$$

wherein R' is H, Cl or —$NH_2$ and m is 1 or 2 and almost no effect of analgesic action was reported.

In the above prior arts, no usefulness of these prior known compounds on apomorphine induced climbing model, a frequently used animal model for schizophrenia, has disclosed.

Creating the specific drug for σ-receptor and finding the novel pharmacological effect are important for developing new type of drugs.

SUMMARY OF THE INVENTION

In the course of screening pharmacological activities of novel synthesized compound, we have found that azepine derivative of the following general formula has high affinity on σ-receptor without indicating affinities on the other receptors, and shows effectiveness for suppressive action of apomorphine induced climbing applied for evaluation of antischizophrenic drug. The present invention has been completed upon he above findings.

An object of the present invention is to provide azepine derivative of the formula $$
\begin{array}{c}
\text{CH}_3 \\
\text{CH}_2\text{---}\text{C*}\text{---}\text{CH}_2 \\
| \quad \quad | \\
\text{H}_3\text{C}\text{---}\text{C}\text{---}\text{CH}_3 \quad \text{N}\text{---}(\text{CH}_2)_m\text{---}\text{R}^1 \\
| \quad \quad | \\
\text{CH}_2\text{---}\text{C*}\text{---}\text{CH}_2 \\
\text{H}
\end{array}
\quad (1)
$$

wherein R is the formula $$\text{R}^1\text{-(CH}_2)_n \quad (2)$$

in which $R^1$ is hydrogen, lower alkyl, lower alkoxy, hydroxy, halogen or optionally substituted phenyl, and n is 0 or 1, cycloalkyl of $C_{5-8}$ which may be substituted by lower alkyl, norbornyl, bicyclo[3.3.1]nonyl, naphthyl, 1,3-benzodioxolyl, pyridyl or thienyl, and m is an integer of 0–4, and C* is asymmetric carbon atom, or nontoxic salt thereof.

Another object of the present invention is to provide a process for producing azepine derivative of the above formula (1) or nontoxic salt thereof comprising reducing a carbonyl of the formula $$
\begin{array}{c}
\text{CH}_3 \\
\text{CH}_2\text{---}\text{C*}\text{---}\text{CH}_2 \\
| \quad \quad | \\
\text{H}_3\text{C}\text{---}\text{C}\text{---}\text{CH}_3 \quad \text{N}\text{---}\text{CO}(\text{CH}_2)_p\text{---}\text{R} \\
| \quad \quad | \\
\text{CH}_2\text{---}\text{C*}\text{---}\text{CH}_2 \\
\text{H}
\end{array}
\quad (3)
$$

wherein C* is asymmetric carbon atom, p is an integer of 0–3, and R has the same meanings hereinbefore, or reacting an amine of the formula $$
\begin{array}{c}
\text{CH}_3 \\
\text{CH}_2\text{---}\text{C*}\text{---}\text{CH}_2 \\
| \quad \quad | \\
\text{H}_3\text{C}\text{---}\text{C}\text{---}\text{CH}_3 \quad \text{N}\text{---}\text{H} \\
| \quad \quad | \\
\text{CH}_2\text{---}\text{C*}\text{---}\text{CH}_2 \\
\text{H}
\end{array}
\quad (4)
$$

wherein C* is asymmetric carbon atom, with a reactive derivative of the formula $$\text{X}\text{---}(\text{CH}_2)_m\text{---}\text{R} \quad (5)$$

wherein X is a reactive organic sulfonyloxy or halogen, m is an integer of 0–4, and R has the same meanings hereinbefore, in inert organic solvent in the presence of base.

Further object of the present invention is to provide a medicament for treatment of diseases participating σ-receptor comprising containing thereof azepine derivative of the formula (1) hereinbefore or nontoxic salt thereof as an active ingredient.

More further object of the present invention is to provide a medicament for treatment of schizophrenia containing azepine derivative of the formula (1) hereinbefore or nontoxic salt thereof as an active ingredient.

Still further object of the present invention is to provide azepine derivatives of the formula (3) or salt thereof hereinbefore, which is useful for an intermediate of azepine derivative of the formula (1) hereinbefore and salt thereof.

BRIEF DESCRIPTION OF THE DRAWING

FIG. 1 shows an X-ray analytical pattern of trans-(1S)-3-[2-(5-hydroxy-2-adamantyl)ethyl]-1,8,8-trimethyl-3-azabicyclo[3.2.1]octane hydrochloride.

DESCRIPTION OF THE PREFERRED EMBODIMENTS

The present invention provides azepine derivatives of the formula

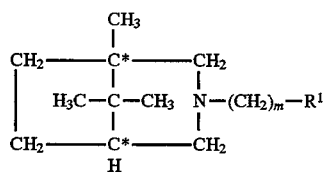

(1)

wherein R is the formula

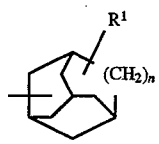

(2)

in which $R^1$ is hydrogen, lower alkyl, lower alkoxy, hydroxy, halogen or optionally substituted phenyl, and n is 0 or 1, cycloalkyl of $C_{5-8}$ which may be substituted by lower alkyl, norbornyl, bicyclo[3.3.1]nonyl, naphthyl, 1,3-benzodioxolyl, pyridyl or thienyl, and m is an integer of 0–4, and C* is asymmetric carbon atom, or nontoxic salt thereof.

Examples of a group R defined in the formula (1) hereinbefore are adamantyl or noradamantyl which is substituted by hydrogen, lower alkyl, lower alkoxy, hydroxy, halogen or optionally substituted phenyl. The above substituents may be substituted in any position of carbon atom in adamantane ring or noradamantane ring. Lower alkyl means alkyl of $C_{1-4}$ which may have branched chain. Lower alkoxy means alkoxy of $C_{1-4}$ which may have branched chain. Halogen means chlorine, bromine, fluorine, etc. Optionally substituted phenyl means phenyl which may be substituted by 1–3 groups of lower alkyl, lower alkoxy, hydroxy or halogen. Binding position of adamantyl and noradamantyl with —(CH$_2$)m- can be at any position of carbon in the said ring.

Examples of the other group R are cycloalkyl of $C_{5-8}$, norbornyl, bicyclo[3.3.1]nonyl, all of which may optionally be substituted by lower alkyl. Binding position of norbornyl and bicyclo[3.3.1]nonyl with —(CH$_2$)m— may be any position of carbon atom in the said ring.

Examples of cycloalkyl of $C_{5-8}$ are cyclopentyl, cyclohexyl, cycloheptyl and cyclooctyl. Lower alkyl means alkyl of $C_{1-4}$ which may have branched chain.

Examples of further different R are naphthyl, 1,3-benzodioxolyl, pyridyl or thienyl. Naphthyl means α-naphthyl or β-naphthyl. 1,3-benzodioxolyl means 1,3-benzodioxol-2-yl, 1,3-benzodioxol-4-yl or 1,3-benzodioxol-5-yl. Pyridyl means 2-pyridyl, 3-pyridyl or 4-pyridyl. Thienyl means 2-thienyl or 3-thienyl.

In case that R in the formula (1) is the group of the formula (2), and $R^1$ is a substituent group other than hydrogen, a stereoisomer will exist depending upon the position of the substituent. In the present invention, not only the mixture of stereoisomer but also the stereoisomer separated by the known method is included in the present invention.

Azepine derivative (1) and nontoxic salt thereof of the present invention can be produced by the following process.

A) Production of the compound (1) wherein m is 1–4, i.e. the compound (1a) of the formula

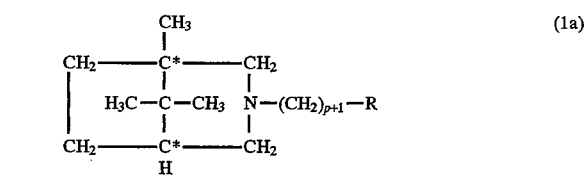

(1a)

wherein C* is asymmetric carbon, p is an integer of 0–3, and R has the same meaning hereinbefore, by reduction of carbonyl in the compound (3).

The compound (3) hereinbefore can be produced by acylating the amine of the formula (4) hereinbefore with a carboxylic acid of the formula

$$R—(CH_2)_p—COOH$$ (6)

wherein p is a integer of 0–3 and R has the same meanings hereinbefore, or reactive derivative thereof.

The above starting material of amine of the formula (4), —i.e. 1,8,8-trimethyl-3-azabicyclo[3.2.1]octane has an asymmetric carbon atom as shown in the formula (4), accordingly, an optical active compound of 1R-configuration or 1S-configuration is used. Compound of 1R-configuration is a known compound and is reported, for example, in Acta Chem. Scand., 17, 2069 (1963) and Tetrahedron Letters, 21, 4593 (1980). Compound of 1S-configuration is unknown compound in the prior references, and can be obtained by reducing (1S)-1,8,8-trimethyl-3-azabicyclo[3.2.1]octane-2-one with reducing agent such as lithium aluminum hydride in an inert organic solvent.

Preferable examples of the carboxylic acid of the formula (6) are 1-adamantyl acetic acid, 2-adamantyl acetic acid, 3-methyl-1-adamantyl, acetic acid, 1-adamantane carboxylic acid, 2-adamantyl-3-propionic acid, 2-adamantyl-4-butyric acid, 3-noradamantane carboxylic acid, 2-norbornyl acetic acid, 9-bicyclo[3.3.1]nonyl acetic acid, cyclohexanecarboxylic acid, cyclopentanecarboxylic acid, cyclopentyl acetic acid, cyclohexyl acetic acid, cycloheptyl acetic acid, cyclooctyl acetic acid, 3-cyclohexylpropionic acid, 4-cyclohexyl butyric acid, 4-methylcyclohexyl acetic acid, 5-hydroxy-2-adamantyl acetic acid, 5-methoxy-2-adamantylacetic acid, 5-phenyl-2-adamantyl acetic acid, 4-hydroxy-2-adamantyl acetic acid and 4-phenyl-2-adamantyl acetic acid. A large number of those are known compounds and can be available commercially or obtainable by synthesis.

A compound including stereoisomer can be used in the form of mixture of stereoisomer or each of the stereoisomer.

Examples of the carboxylic acid of the formula (6) are α-naphthyl acetic acid, βnaphthyl acetic acid, 1,3-benzodioxol-2-acetic acid, 1,3-benzodioxol-4-acetic acid, 1,3-benzodioxol-5-acetic acid, 2-pyridyl acetic acid, 3-pyridyl acetic acid, 4-pyridyl acetic acid, 2-thienyl acetic acid and 3-thienyl acetic acid. These are known compounds—and can be obtained commercially or by synthesis.

The above acylation reaction can be performed by known amidation reaction. Free form of the carboxylic acid (6) can be used in the presence of condensing agent. Examples of the condensing agent are carbodiimides such as N,N-dicyclohexylcarbodiimide (DCC), 1-ethyl-3(3'-dimethylaminopropyl) carbodiimide (WSC) and N-cyclohexyl-N'-(4-diethylaminocyclohexyl) carbodiimide, a reagent such as diphenylphosphoryl azide, benzotriazolyl-N-hydroxy tris (dimethylamino)phosphonium hexafluorophosphate and carbonyldiimidazole, and a reagent (Vilsmeier reagent) which is synthesized by a reaction of amide compound such as N-methylformamide or N,N-dimethylformamide with halide such as thionyl chloride, phosphorus chloride or phosgene. The other known condensing agent can be used.

Examples of reactive derivative of the carboxylic acid (6) are halide thereof, acid anhydride, acid azide, activated ester and activated amide. Preferable examples are acid chloride and acid bromide, mixed anhydride with acetic acid, pivalic acid, isovaleric acid, trichloroacetic acid and carboxylate monoalkyl ester, activated ester such as P-nitrophenyl ester, 2,4-dinitrophenyl ester, trichlorophenyl ester, pentachlorophenyl ester, 1-hydroxy-1H-pyridone, N-hydroxysuccinimide ester and N-hydroxyphthalimide ester, and activated amide of pyrazole, imidazole, dimethylpyrazole or benzotriazole.

A reaction using acid halide or acid anhydride of reactive derivative in the above acylating reaction is preferably performed in the presence of deacidification reagent. Examples of deacidification reagent are tertiary amine such as triethylamine, ethyldiisopropylamine, N,N-dimethylaniline, N-methylmorpholine and pyridine, or known inorganic base.

An amount of ratio in amine (4) and carboxylic acid (6) or reactive derivative thereof is theoretically equimolar, however carboxylic acid (6) or reactive derivative may be used in excess.

Acylating reaction hereinabove is proceeded in an organic solvent which does not effect detrimental effect. Examples of organic solvent are chloroform, methylene chloride, tetrahydrofuran, 1,4-dioxane, N,N-dimethylformamide, N,N-dimethylacetamide and acetone, or mixed solvent thereof. Reaction temperature is not specifically limited, and reaction is usually proceeded at room temperature. Reaction time depends upon reaction temperature and carboxylic acid (6) or reactive derivative thereof and can not be specified, but is at most up to 48 hours.

Isolating of the compound (3) produced by acylating reaction hereinabove from reaction mixture can be performed by that, in case of reaction solvent being water immiscible organic solvent, after the reaction mixture is washed with aqueous alkaline solution, aqueous acidic solution or saturated sodium chloride solution, organic solvent layer is collected and concentrated, or in case of reaction solvent being water miscible organic solvent, after removal of the solvent, the residue is dissolved in water immiscible organic solvent, then treated the same as of the above to obtain the compound (3). The compound (3) can be purified by known conventional means such as column chromatography and recrystallization.

In case that the compound (3) includes stereoisomer, and when a stereoisomer mixture of the carboxylic acid (6) is used, the compound(3) can be obtained in the form of stereoisomer mixture, and when each stereoIsomer of the carboxylic acid (6) is used, the compound (3) can be obtained in the form of each corresponding stereoisomer.

In the present invention, carbonyl group of the compound (3) is reduced to obtain the compound (1a) of the present invention. The reaction can be performed by reducing the compound (3) in inert organic solvent with reducing agent such as lithium aluminum hydride, sodium aluminum hydride and boron hydride. Examples of inert organic solvent are tetrahydrofuran, diethyl ether, 1,4-dioxane and pyridine. Reaction temperature is usually under heating preferably with reflux condition. Reaction time depends on reaction temperature, type of reducing agent, and the reaction can be checked by means of thin layer chromatography or high performance liquid chromatography, accordingly the reaction can be terminated by observing disappearing the compound (3). The reaction time is, not specified, approximately 1–10 hours.

The compound (1a) produced by reduction reaction hereinabove can be isolated from the reaction mixture by, in case of reaction solvent being water immiscible organic solvent, after washing the reaction mixture with aqueous acidic solution, aqueous alkaline solution or aqueous saturated sodium chloride solution, concentrating the organic solvent layer, and, in case of reaction solvent being water miscible solvent, after removing the solvent by distillation, and if required dissolving the residue in water immiscible organic solvent, and treating the mixture as same as of the above, to obtain the compound (1a). The compound (1a) can be purified further, for example, by conventional known purification method such as column chromatography and recrystallization.

In the present invention, in case that a mixture of stereoisomer of the compound (3) is used and the product is obtained by means of the above reducing reaction, the compound (1a) of the stereoisomer can be obtained by the following isolation method.

The product can be isolated, for example, by a known method including silica-gel column chromatography and high performance liquid chromatography, both of which has an ability to isolate each stereoisomer (stereoisomeric compound). The isolation of the stereoisomer (stereoisomeric compound) depend upon a type of substituent of R in the compound (1a), a position of the substitution, a type of carrier such as silica-gel, a type of isolating solvent and ratio of the solvent.

Further, in the synthetic processes hereinbelow, in case that a starting material of a mixture of stereoisomer (stereoisomeric compound) is used as like the process hereinabove, the produced compound is used as like the process hereinabove, the produced compound (1), (1c), (1d) or (1e) hereinbelow requires to isolate to each stereoisomer. Another embodiment of the invention is a stereoisomeric compound of formula

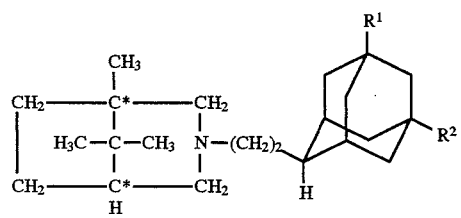

wherein one of $R^1$ and $R^2$ is hydrogen and the other is hydroxy, lower alkoxy, halogen or phenyl and C* is an asymmetric carbon, and nontoxic salts thereof.

B) Production of the compound (1) by N-alkylation of the amine (4)

A compound (1) can be produced by reacting an amine of the formula

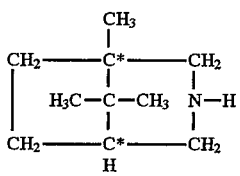

(4)

wherein C* asymmetric carbon atom, with a reactive derivative of the formula $$X-(CH_2)_m-R \quad (5)$$

wherein X is reactive organic sulfonyloxy or halogen, m is an integer of 0–4, and R has the same meanings hereinbefore, in an inert organic solvent in the presence of base.

Sulfonyloxy derivative in the reactive derivative (5) hereinabove can be produced by sulfonylation of alcohol of the formula $$HO-(CH_2)_m-R \quad (7)$$

wherein m is an integer of 0–4, with methanesulfonyl chloride or P-toluenesulfonyl chloride in a dry inert solvent such as methylene chloride.

Examples of the alcohol (7) hereinabove are 1-adamantyl ethanol, I-adamantyl methanol, 2-adamantyl ethanol-2-norbornyl ethanol, 3-noradamantyl methanol, 9-bicyclo [3.3.1]nonyl ethanol, cyclopentyl alcohol, cyclohexyl alcohol, cyclopentyl methanol, cyclohexyl methanol, cycloheptyl methanol, cyclooctyl methanol, cyclopentyl ethanol, cyclohexyl ethanol, cycloheptyl ethanol, 3-cyclohexyl-1-propanol, 4-cyclohexyl-1-butanol, 5-methoxy-2-adamantyl ethanol, 5-chloro-2-adamantyl ethanol, 5-phenyl-2-adamantyl ethanol and 4-phenyl-2-adamantyl ethanol. These compounds are known compound and can be obtainable commercially or by synthesis.

Stereoisomer of these compounds, if exist, can be used in the form of a mixture of the stereoisomer or each corresponding stereoisomer.

Examples of the other alcohol (7) are α-naphthyl ethanol, β-naphthyl ethanol, 1,3-benzodioxole-2-ethanol, 1,3-benzodixole-4-ethanol, 1,3-benzodixole-5-ethanol, 2-pyridyl ethanol, 3-pyridyl ethanol, 4-pyridyl ethanol, 2-thienyl ethanol and 3-thienyl ethanol. These compounds are known compounds and can be obtainable commercially or by synthesis.

Halogenated examples of the reactive derivative (5) are cyclohexyl bromide, cyclohexylmethyl bromide, I-adamantyl bromide and 2-adamantyl bromide. These compounds are known compounds which are listed in the catalogue of the reagents' manufacturer, and can be obtainable.

Further halogenated examples of the reactive derivative (5) hereinabove are α-naphthylethyl bromide, β-naphthylethyl bromide, 1,3-bezodioxole-2-ethyl bromide, 1,3-benzodioxole-4-ethyl bromide, 1,3-benzodioxole-5-ethyl bromide, 2-pyridylethyl bromide, 3-pyridylethyl bromide, 4-pyridylethyl bromide, 2-thienylethyl bromide and 3-thienylethyl bromide.

Examples of base used in a reaction of amine (4) and reactive derivative (5) are, for example, tertiary organic base such as triethylamine, ethyldiisopropylamine, N,N-dimethylaniline, N-methylmorpholine, pyridine and N,N-dimethylaminopyridine, and inorganic base such as carbonate, hydrogen carbonate, hydroxide or hydride of alkaline metal or alkaline earth metal.

Examples of inert organic solvent used in the reaction hereinbefore are acetonitrile, benzene, acetone and tetrahydrofuran, and acetonitrile is most preferable. The above reaction proceeds, usually, at reflux temperature of the reaction solvent used. Reaction time depends on a reaction temperature or base, and reaction progress can be checked by thin layer chromatography or high performance liquid chromatography, and the reaction can be terminated by checking disappearance of amine (4). Reaction time is, not specified, approximately 2–72 hours.

Isolation of the compound (1) from reaction mixture hereinbefore can be performed by filtering insoluble material, concentrating the solvent, and purifying the residue by conventional silica-gel column chromatography with the developer of mixture of chloroform and acetone or methanol.

C) Production of the compound (1) wherein $R^1$ is halogen, i.e. a compound (1c) of the formula

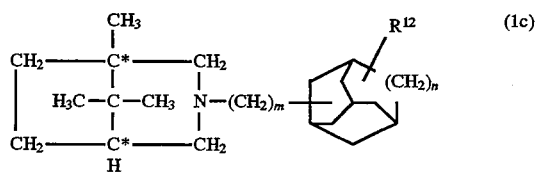

(1c)

wherein $R^{12}$ is halogen, and C* m and n have the same meanings hereinbefore:

A compound (1c) can be produced by halogenating the compound (1b) of the formula

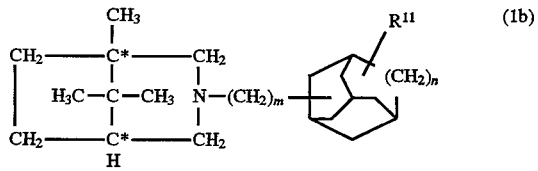

(1b)

wherein $R^{11}$ is hydroxy, and C*, m and n have the same meanings hereinbefore.

The above halogenation reaction can be performed by the known halogenating reaction. Examples of the halogenating agent are thionyl chloride, phosphorus trichloride, phosphorus pentachloride, hydrochloric acid, phosphorus oxychloride, hydrobromic acid and diethylamino sulphur trifluoride (DAST). Reaction can be proceeded without solvent or in an inert organic solvent. Another halogenating agent can also be used.

In the above halogenating reaction, reaction temperature is not limited and depends on a type of halogenating agents, preferably at room temperature to reflux temperature. The reaction time depends on a type of halogenating agents and is, not specified, approximately 48 hours.

Isolation of the compound (1c) from reaction mixture depends on a type halogenating agents, and can be preformed by concentrating the reaction mixture, adding water or pouring the reaction mixture to an ice-water, adjusting the aqueous layer to alkaline pH, extracting with organic solvent such as dichloromethane and concentrating the organic layer to obtain the compound (1c).

D) Production of the compound (1) wherein $R^1$ is lower alkoxy, i.e. a compound (1d) of the formula

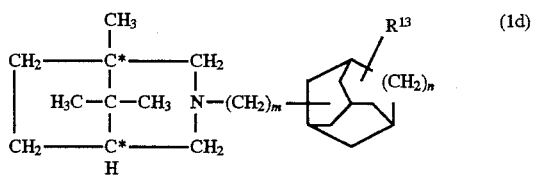

wherein $R^{13}$ is lower alkoxy, and C*, m and n have the same meaning hereinbefore:

The compound (1d) can be prepared by alkylating the compound (1b). The above alkylating reaction can be performed by a known alkylating reaction. Example of alkylating reaction is a reaction using alkyl halide in an inert organic solvent in the presence of deacidification reagent. Examples of deacidification reagent are known tertiary organic bases such as triethylamine, ethyl diisopropylamine, N,N-dimethylaniline, N-methylmorpholine and pyridine, and known inorganic base such as sodium hydroxide, sodium hydride and sodium amide. Examples of alkylhalide are methyl iodide, ethyl iodide, propyl iodide, butyl iodide, isopropyl iodide, isobutyl iodide, bromoethane, 1-bromopropane, 2-bromopropane, 1-bromobutane, 2-bromobutane, 1-chloropropane, 2-chloropropane, 1-chlorobutane and 2-chlorobutane. Examples of inert organic solvent are 1,2-dimethoxyethane (DME), THF, dimethylsulfoxide (DMSO) and DMF or mixture thereof. Ratio of the amount of the compound (1b) and alkyl halogenate is theoretically in equimolar, and conventionally excess amount of alkyl halide is used.

Reaction temperature in the alkylation reaction hereinabove is not limited and is proceeded at room temperature. Reaction time depends on reaction temperature and type of alkyl halide, and is, not specified, approximately 48 hours.

Isolation of the compound (1d) from the reaction mixture can be made by, in case of the reaction solvent being water immiscible organic solvent, after washing the reaction mixture with aqueous alkali or saturated sodium chloride solution, and concentrating the organic solvent, or in case of the reaction solvent being water miscible organic solvent, removing the organic solvent, dissolving the residue in water immiscible organic solvent, and treating as same as of the above to obtain the compound (1d). Another alkylating reagent such as dimethyl sulfate can also be used.

E) A compound (1) wherein $R^1$ is phenyl, i.e. the compound (1e) of the formula

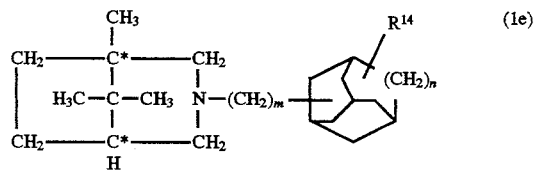

wherein $R^{14}$ is phenyl and C*, m and n have the same meanings hereinbefore:

The compound (1e) can be produced by phenylating the compound (1b) or (1c).

The above phenylating reaction can be performed by known phenylating reaction. Example of the above phenylating reaction is preferably Friedel-Crafts reaction, in which the compound is reacted with benzene in an inert organic solvent in the presence of Lewis acid of aluminum chloride or aluminum bromide or protonic acid. Examples of inert organic solvent are dichloromethane, nitromethane, carbon disulfide and acetonitrile, or mixture thereof. Benzene can be used as a solvent.

Reaction temperature in the above phenylating reaction is not limited and is proceeded at room temperature to 100° C. Reaction time depends on a reaction temperature, and is, not specified, approximately 24 hours.

Isolation of the compound (1e) from the reaction mixture can be performed by pouring the reaction mixture into ice-water, adjusting the aqueous layer to alkaline condition, extracting with organic solvent such as dichloromethane and concentrating the organic layer to obtain Another type of phenylating reaction can also be applied.

In the present invention, when a compound of the present invention (1) is disclosed, the compound can easily be synthesized by combining prior known reactions other than the process hereinabove explained.

The thus produced compound of the present invention (1) can be converted, if required, to a pharmaceutically acceptable nontoxic salt thereof.

Examples of those salts are acid addition salt, and are inorganic salt of hydrochloride, sulfate and phosphate, and organic salt of acetate, propionate, tartrate, citrate, glycolate, gluconate, succinate, malate, glutamate, aspartate, methanesulfonate, mandelate, p-toluenesulfonate and maleinate.

The compound of the present invention (1) or nontoxic salt thereof showed no death in an intravenous administration of 30 mg/kg to rat and the compound can be said quite safety to use as a medicament.

The compound of the present invention or nontoxic salt thereof is used in the form of formulation and is administered per oral or parenterally such as injection including drop infusion. An amount of administration may be varied by dosage form, age, body weight and condition of recipients, and is 0.1 mg–100 mg/adult/day.

A preparations of the above formulation are tablets, pills, powders, granules, capsules and injectable form. Production of the formula can be made by adding various kinds of carriers, for example fillers such as starch, lactose, sugars, mannitol, carboxymethyl cellulose, corn starch or inorganic salt, binders such as starch, dextrin, arabic gum, gelatin, hydroxypropyl starch, methylcellulose, sodium carboxymethyl cellulose, hydroxypropyl cellulose, crystalline cellulose, ethyl cellulose, polyvinylpyrrolidone and macrogol, disintegrators such as starch, hydroxypropyl starch, carboxypropyl starch, sodium carboxymethyl cellulose and hydroxypropyl cellulose, surface active agents such as sodium lauryl sulfate, soybean lecithin, sucrose fatty acid ester and polysorbate 80, lubricants such as talc, wax, hydrogenated vegetable oil, sucrose fatty acid ester, magnesium stearate and calcium stearate, fluidity stimulant, correctives, coloring agents and perfume.

The compound of the present invention (1) or nontoxic salt thereof can be made suspension, emulsion, syrup or elixirs. Parenteral formulation can be contained as diluting agent such as injectable distilled water, physiological saline, glucose solution, injectable vegetable oil, propylene glycol and polyethyleneglycol. If necessary, bactericides, antiseptics, stabilizers, tonicity agents and soothing agents.

Binding activities of a compound of the present invention (1) or nontoxic salt thereof to σ-receptor are assayed by the following methods. Results are shown Tables I and 2.

(A) Binding activities of the compound of the present invention on σ-receptor are assayed by a method described in E. Weber et al, Proc. Natl. Acad. Sci. U.S.A. vol. 83, 8784–8788 (1986).

Immediately after decapitation of Sprague-Dowley rat, male, 7 weeks age, supplied by Charles River Inc., brains were collected and whole brains except cerebella were homogenized with 50 mM Tris-HCL buffer solution (PH 8.0, TH buffer solution) and centrifuged at 700× g for 10 minutes. The supernatant was centrifuged at 48,000× g for 15 minutes, and precipitates were suspended in TH buffer solution which was incubated at 37° C. for 20 minutes. The suspension was centrifuged at 48,000× g for 15 minutes and the thus obtained precipitates were suspended in TH buffer solution to prepare a membrane standard preparation.

The standard preparation of membrane (approx. 600 μg protein) and [$^3$H]1,3-di (2-tolyl) guanidine (DTG, New England Nuclear Corp.) (final concentration: 3 nM) were reacted at 25° C. for 60 minutes, and the reaction was stopped by suction filtering through Whatman GF/C filter.

Radioactivity adsorbed on the filter was measured by Scintillation Counter, and the value obtained was set as total binding amount. Non specific binding amount (NB) was set up by measuring the assay mixture with adding 10 kiM haloperidol. Binding assay of the sample was performed by adding the sample in place of adding haloperidol in the assay system to obtain the assaying result (DTB).

(B) Ki-value (affinity of the drug to receptor)

Binding inhibitory rate of the sample at constant concentration was calculated by the following equation.

Binding inhibition rate (%)=(1−(DTB−NB)÷(TB−NB))×100

Binding inhibition rates at various concentrations from high to low concentrations were measured in each sample, and plotted a logarithmic value of concentration on a transverse and binding inhibition rate on an ordinate, then drawing a curve by the nonlinear method of least squares to obtain $IC_{50}$ value.

Ki value is calculated by the following equation.

$Ki=(IC_{50})÷(1+(L)/Kd)$ wherein (L) is a concentration of radioactive ligand (3 nM) in the experiment, Kd is concentration of the affinity of radioactive ligand for receptor (10.6 nM) and $IC_{50}$ is a concentration of drug which inhibits at 50% for binding receptor and radioactive ligand.

TABLE 1

| Binding activity for σ-receptor | |
|---|---|
| Compound numbered in Examples (hydrochloride | Sigma [$^3$H] DTG Ki (nM) |
| 1 | 0.26 |
| 2 | 0.39 |
| 3 | 0.53 |
| 4 | 0.28 |
| 6 | 0.16 |
| 7 | 0.57 |
| 8 | 0.50 |
| 9 | 3.72 |
| 10 | 0.92 |
| 11 | 3.63 |
| 12 | 2.53 |
| 13 | 6.37 |
| 14 | 0.32 |
| 15 | 0.32 |
| 16 | 0.32 |
| 18 | 2.23 |
| 19 | 0.87 |
| 20 | 4.16 |
| 21 | 0.88 |
| 23 | 0.44 |
| 24 | 0.67 |
| 25 | 0.58 |
| 27 | 1.60 |

TABLE 2

| Binding activity for σ-receptor | |
|---|---|
| Compound numbered in Examples (hydrochloride | Sigma [$^3$H] DTG Ki (nM) |
| 45 | 2.22 |
| 46 | 8.57 |
| 47 | 16.10 |
| 48 | 15.05 |
| 49 | 9.00 |
| 50 | 28.32 |
| 51 | 31.82 |
| 52 | 79.54 |
| 53 | 21.50 |
| 54 | 13.35 |
| 55 | 7.04 |
| 58α | 2.4 |
| 58β | 0.28 |
| 60β | 0.79 |
| 63 | 0.95 |
| 66β | 2.4 |

As shown hereinabove, the compound of the present invention (1) or nontoxic salt thereof has strong affinity to σ-receptor and has no affinity to the other receptors.

Pharmacological action of the compound of the present invention (1) is explained hereinbelow.

Suppressive activity of apomorphine induced climbing

Administering dopamine agonist, apomorphine in mouse resulted various abnormal movings, and especially, a climbing the cage has been known to be correlated with human schizophrenia. Therefore, a drug showing suppressive activity for apomorphine induced climbing in mice can be presumed to be effective as antischizophrenia activity on humans.

Compounds of the present invention were administered orally or intraperitoneally in ICR mice, male (Charles River Corp.), and after 30 minutes apomorphine 2 mg/kg was administered subcutaneously. Climbing behaviors of 3 minutes after 20–23 minutes of apomorphine administration were observed. Climbing behavior was observed by entering the mice in stainless steel made wire netting cage and measuring a time remaining above the upper part of half part of the cage at observing. A climbing time of apomorphine single administered group is set as 100% and shortened time by administering the drug is shown in suppression rate.

TABLE 3

| Suppressive action on apomorphine induced climbing | |
|---|---|
| Sample | Suppression rate (mg/kg, p.o) |
| Compound numbered as Example No. | |
| 1 (hydrochloride) | 37% (30) |
| 15 (hydrochloride) | 78% (10) |
| 16 (hydrochloride) | 79% (30) |
| 21 (hydrochloride) | 54% (30) |
| 23 (hydrochloride) | 69% (10) |
| 24 (hydrochloride) | 78% (10) |
| 25 (hydrochloride) | 43% (30) |
| 28 (hydrochloride) | 74% (30) |

TABLE 4

| Suppressive action on apomorphine induced climbing | |
|---|---|
| Sample | Suppression rate (mg/kg, i.p.) |
| Compound numbered as Example No. | |
| 46 (hydrochloride) | 45% (10) |
| 50 (hydrochloride) | 50% (1) |
| Control | 40% (1) |
| Chlorpromazine | |

| Sample | Suppression rate (mg/kg, p.o.) |
|---|---|
| 58α (hydrochloride) | 75% (30) |
| 58β (hydrochloride) | 83% (10) |

As shown in Tables 3 and 4, the compound of the present invention (1) suppressed apomorphine induced climbing. These results indicated that the compound of the present invention (1) has strong anti schizophrenia activity.

As clearly shown in the experimental results hereinbefore, the compound of the present invention (1) or nontoxic salt thereof has strong affinity to σ-receptor without showing affinity to the other receptors. Further the compound is effective for suppressing apomorphine induced climbing, which is used for evaluation of schizophrenia, therefore, it is useful for treatment of the diseases relating to σ-receptor, for example treatment of schizophrenia.

EXAMPLES

The present invention is explained in details by the referential examples and examples hereinbelow, however the present invention is not limited within these examples. Mass spectrum (MS) data and Nuclear Magnetic Resonance spectrum data ($^1$H-NMR) of the compounds obtained by these examples are shown in Tables 5–8.

Rf values of TLC in the examples are measures, if not specified, by using the following carrier and developer Carrier: Merck, TLC plate silica gel 60F$_{254}$, Art 5715

Developer: chloroform: ethanol=5:1

Referential Example 1

Production of (1S)-1,8,8-trimethyl-3-azabicyclo[3.2.1]octan-2-one: (1S)-camphor 8.31 g and hydroxylamine-O-sulfonic acid 9.25 g in acetic acid 200 ml were refluxed under heating for 7 hours. The reaction mixture was concentrated in vacuo and the residue dissolved in chloroform was washed with saturated aqueous sodium bicarbonate solution. Organic layer was dried by anhydrous sodium sulfate, which was thereafter removed by filtration, then the filtrate was concentrated in vacuo. The thus obtained residue was purified by means of silica gel column chromatography (Wako gel™, C200, chloroform) to obtain the product.

Yield: 5.57 g (Yield 56%)

$[\alpha]_D^{25}$=+25.0° (c=1, methanol)

Referential Example 2

Production of (1S)-1,8,8-trimethyl-3-azabicyclo[3.2.1]octane:

(1S)-1,8,8-trimethyl-3-azabicyclo[3.2.1]octan-2-one 1.93 g was added in tetrahydrofuran (THF) 20 ml solution of lithium aluminum hydride 0.88 g, and the reaction mixture was refluxed under heating for 22 hours. The reaction mixture was cooled and added 6N HCL and 5N NAOH therein to alkalize the mixture. Insoluble material was filtered and the filtrate was extracted with diethyl ether (ether), dried by anhydrous sodium sulfate, which was thereafter removed by filtration, then the filtrate was concentrated in vacuo to obtain the product.

Yield: 1.70 g (Yield 97%)

$[\alpha]_D^{25}$=+17.2° (c=1, methanol)

Example 1

Production of (1S)-3-[2-(1-adamantyl)ethyl]-1,8,8-trimethyl-3-azabicyclo[3.2.1]octane:

Triethylamine 0.43 ml was added in a methylene chloride 20 ml solution of (1S)-1,8,8-trimethyl-3-azabicyclo[3.2.1]octane hydrochloride 490 mg, and stirred at 0° C. for 1 hour. 1-adamantyl acetic acid 552 mg and 1-ethyl-3-(3'-dimethylaminopropyl) carbodiimide hydrochloride (WSC) 595 mg were added therein, then the reaction mixture was gradually changed to room temperature and stirred for 23 hours. The reaction mixture was washed with 10% sodium hydroxide and dried by anhydrous sodium sulfate. After filtering the drying agent, the filtrate was concentrated in vacuo to obtain crude (1S)-3-(1-adamantylacetyl)-1,8,8-trimethyl-3-azabicyclo[3.2.1]octane. The concentrate was added to THF 25 ml solution of lithium aluminum hydride 196 mg and refluxed for I hour. The reaction mixture was cooled, then added ether, water and 10% aqueous sodium hydroxide thereto, and filtered the insoluble material. The filtrate was extracted with ether and dried by anhydrous sodium sulfate. After filtering the drying agent, a residue obtained by concentrating the filtrate in vacuo was purified by means of flash column chromatography (Merck, silica gel 60: 230–600 mesh, chloroform) to obtain the product. Yield: 737 mg (Yield 91%)

Two excess molar amount of methanol solution of hydrogen chloride was added to the thus obtained product, concentrated and crystallize by adding diethyl ether to obtain the hydrochloride.

$[\alpha]_D^{25}$=−8.6° (c=0.5, methanol)

Example 2

Production of (1S)-3-[2-(2-norbornyl)ethyl]-1,8,8-trimethyl-3-azabicyclo[3.2.1]octane:

Triethylamine 0.43 ml was added in a methylene chloride 20 ml solution of (1S)-1,8,8-trimethyl-3-azabicyclo[3.2.1]octane hydrochloride 485 mg, and stirred at 0° C. for 40 min. 2-norbornyl acetic acid 0.41 ml and WSC 588 mg were added therein, then the reaction mixture was gradually changed to room temperature and stirred for 23 hours. The reaction mixture was concentrated in vacuo and the concentrate was dissolved in ether, then washed with 5N sodium hydroxide and dried by anhydrous sodium sulfate. After filtering the drying agent, the filtrate was concentrated in vacuo to obtain crude (1S)-3-(2-norbornylacetyl)-1,8,8-trimethyl-3-azabicyclo[3.2.1]octane. The concentrate was added to THF 20 ml solution of lithium aluminum hydride 194 mg and refluxed for I hour. The reaction mixture was cooled, then added ether, water and 10% aqueous sodium hydroxide thereto, and filtered the insoluble material. The filtrate was extracted with ether and dried by anhydrous sodium sulfate. After filtering the drying agent, a residue obtained by concentrating the filtrate in vacuo was purified by means of flash column chromatography (Merck, silica gel 60: 230–600 mesh, chloroform-chloroform:acetone=20:1) to obtain the product. Yield: 618 mg (Yield 88%)

The product was treated by the same way as of in Example I to obtain the hydrochloride.

$[\alpha]_D^{25}=-11.3°$ (c=0.5, methanol)

Example 3

Production of (1S)-3-(2-cyclopentylethyl)-1,8,8-trimethyl-3-azabicyclo[3.2.1]octane:

Triethylamine 0.43 ml was added in a methylene chloride 20 ml solution of (1S)-1,8,8-trimethyl-3-azabicyclo[3.2.1]octane hydrochloride 0.49 g, and stirred at 0° C. for 45 min. Cyclopentyl acetic acid 0.36 ml and WSC 0.59 g were added therein, then the reaction mixture was gradually changed to room temperature and stirred for 24 hours. The reaction mixture was washed with 10% sodium hydroxide and dried by anhydrous sodium sulfate. After filtering the drying agent, the filtrate was concentrated in vacuo to obtain crude (IS)-3-cyclopentylacetyl-1,8,8-trimethyl-3-azabicyclo[3.2.1]octane. The concentrate was added to THF 30 ml solution of lithium aluminum hydride 0.19 g and refluxed for 1.5 hours. The reaction mixture was cooled, then added ether, water and 10% aqueous sodium hydroxide thereto, and filtered the insoluble material. The filtrate was extracted with ether and dried by anhydrous sodium sulfate. After filtering the drying agent, a residue obtained by concentrating the filtrate in vacuo was purified by means of flash column chromatography (Merck, silica gel 60: 230–600 mesh, chloroform-chloroform:acetone=20:1) to obtain the product.

Yield: 0.58 g (Yield 91%)

The product was treated by the same way as of in Example 1 to obtain the hydrochloride.

$[\alpha]_D^{25}=-11.8°$ (c=0.5, methanol)

Example 4

Production of (1S)-3-(2-cyclohexylethyl)-1,8,8-trimethyl-3-azabicyclo[3.2.1]octane:

Triethylamine 0.84 ml was added in a methylene chloride 20 ml solution of (1S)-1,8,8-trimethyl-3-azabicyclo[3.2.1]octane hydrochloride 0.95 g, and stirred at o@C for 30 min. Cyclohexyl acetic acid 0.72 g and WSC 1.35 g were added therein, then the reaction mixture was gradually changed to room temperature and stirred for 25 hours. The reaction mixture was washed with saturated sodium chloride solution and dried by anhydrous sodium sulfate. After filtering the drying agent, the filtrate was concentrated in vacuo to obtain crude (IS)-3-cyclohexylacetyl-1,8,8-trimethyl-3-azabicyclo[3.2.1]octane. The concentrate was added to THF 30 ml solution of lithium aluminum hydride 0.38 g and refluxed for 1 hour. The reaction mixture was cooled, then added 6N hydrochloric acid and 1N sodium hydroxide thereto, and filtered the insoluble material. The filtrate was concentrated in vacuo. The thus obtained residue was purified by means of silica gel column chromatography (Wako gel, $C_{200}$, chloroform acetone methanol=10:1:0.1) to obtain the product.

Yield: 1.01 g (Yield 77%)

The product was treated by the same way as of in Example 1 to obtain the hydrochloride.

$[\alpha]_D^{25}=-11.5°$ (c=0.5, methanol)

Example 5

Production of (1R)-3-cyclohexylacetyl-1,8,8-trimethyl-3-azabicyclo[3.2.1]octane:

Triethylamine 0.84 ml was added in a methylene chloride 20 ml solution of (1R)-1,8,8-trimethyl-3-azabicyclo[3.2.1]octane hydrochloride 0.95 g, and stirred at O@C for 30 min. Cyclohexyl acetic acid 0.72 g and WSC 1.35 g were added therein, then the reaction mixture was gradually changed to room temperature and stirred for 24 hours. The reaction mixture was washed with saturated sodium chloride and dried by anhydrous sodium sulfate. After filtering the drying agent, a residue obtained by concentrating the filtrate in vacuo was purified by means of silica gel column chromatography (Wako gel, C200, chloroform:methanol=50:1) to obtain the product.

Yield: 0.52 g (Yield 37%)

Example 6

Production of (1R)-3-(2-cyclohexylethyl)-1,8,8-trimethyl-3-azabicyclo[3.2.1]octane:

(IR)-3-cyclohexylacetyl-1,8,8-trimethyl-3-azabicyclo[3.2.1]octane 0.52 g was added to THF 20 ml solution of lithium aluminum hydride 0.15 g and refluxed for 1 hour. The reaction mixture was cooled, then added water thereto, and filtered the insoluble material. The filtrate was concentrated in vacuo. The thus obtained residue was purified by means of silica gel column chromatography (Wako gel, C200, chloroform:acetone:methanol 5:1:0.1) to obtain the product.

Yield: 0.30 g (Yield 61%)

The product was treated by the same way as of in Example 1 to obtain the hydrochloride.

$[\alpha]_D^{25}=+11.6°$ (c=0.5, methanol)

Referential Example 3

Production of methyl cycloheptylidene acetate:

Cycloheptanone 1.18 ml and methyl diethylphosphonoacetate 2.21 ml were dissolved in benzene 10 ml, and sodium hydride (60%, oil dispersion) 0.08 g was added thereto, then stirred at room temperature for 15 hours, thereafter refluxed under heating for 6 hours. Water was added to the reaction mixture and extracted with chloroform, then dried by anhydrous sodium sulfate. The drying agent was removed by filtration and the filtrate was concentrated in vacuo. The thus obtained residue was purified by means of silica gel column chromatography (Wako gel, C200, chloroform) to obtain the product.

Yield: 1.20 g (Yield 71%)

Referential Example 4

Production of cycloheptylethyl alcohol:

Methyl cycloheptylidene acetate 1.20 g was added in THF 35 ml solution of lithium aluminum hydride 0.81 g, and the reaction mixture was refluxed under heating for 4 hours. The reaction mixture was cooled, and added water and 10% sodium hydroxide therein, then insoluble material was filtered. The filtrate was extracted with ether and dried by anhydrous sodium sulfate. After removing the drying agent by filtration, the filtrate was concentrated in vacuo. The concentrate was dissolved in methanol 50 ml, added 10% Pd-C 0.12 g, and being subjected to catalytic hydrogenation under hydrogen atmosphere at normal temperature and normal pressure for 4 hours. Thereafter Pd-C was filtered and the filtrate was concentrated in vacuo to obtain the product.

Yield: 0.45 g (Yield 45%)

Example 7

Production of (IS)-3-(2-cycloheptylethyl)-1,8,8-trimethyl-3-azabicyclo[3.2.1]octane:

Cycloheptylethyl alcohol 0.45 g was dissolved in methylene chloride 20 ml and cooled to 0° C., then methanesulfonyl chloride 0.30 ml and triethylamine 0.62 ml were added thereto. Temperature of the reaction mixture was gradually changed to room temperature and stirred for 22 hours. The reaction mixture was concentrated in vacuo to obtain the crude mesylate. (IS)-1,8,8-trimethyl-3-azabicyclo[3.2.1]octane hydrochloride 0.51 g and potassium carbonate 1.10 g were added thereto, then prepared acetonitrile 20 ml solution. The solution was refluxed under heating for 24 hours. Insoluble material was removed by filtration and the filtrate was concentrated in vacuo. The thus obtained residue was purified by means of flash column chromatography (Merck silica gel 60: 230–600 mesh, chloroform) to obtain the product.

Yield: 0.61 g (Yield 82%)

The product was treated by the same way as of in Example 1 to obtain the hydrochloride.

$[\alpha]_D^{25}=-11.7°$ (c=0.5, methanol)

Referential Example 5

Production of methyl cyclooctylidene acetate:

Cyclooctanone 2.00 g and methyl diethylphosphonoacetate 3.50 ml were dissolved in THF 20 ml, and the solution was cooled to 0° C. Tertiary butanol 10 ml solution of potassium tertiary butoxide 2.67 g was added dropwise for 20 minutes. Temperature of the reaction mixture was gradually changed to room temperature and stirred for 12 hours. Water was added to the reaction mixture and THF was removed by concentration in vacuo. The thus obtained residue was extracted with ethyl acetate and dried by anhydrous sodium sulfate. The drying agent was removed by filtration and the filtrate was concentrated in vacuo. The thus obtained residue was purified by means of silica gel column chromatography. (Wako gel, C200, chloroform) to obtain the product.

Yield: 1.33 g (Yield 46%)

Referential Example 6

Production of cyclooctyl acetic acid methyl ester:

Methyl cyclooctylidene acetate 0.50 g was dissolved in methanol 5 ml, added 10% Pd-C 0.10 g thereto, and being subjected to catalytic hydrogenation under hydrogen atmosphere at normal temperature and normal pressure for 3 hours. Thereafter Pd-C was filtered and the filtrate was concentrated in vacuo to obtain the product.

Yield: 0.45 g (Yield 88%)

Referential Example 7

Production of cyclooctyl acetic acid:

Cyclooctyl acetic acid methyl ester 0.45 g was dissolved in methanol 10 ml, added 1N sodium hydroxide 4.0 ml thereto and stirred at room temperature for 7 hours. Then reaction mixture was concentrated in vacuo. Saturated aqueous sodium bicarbonate was added to the residue and the mixture was washed with ether. Aqueous layer was cooled, acidified by adding 6N hydrochloric acid and extracted with ethylacetate. The extract was dried by anhydrous sodium sulfate. After removing the drying agent by filtration, the filtrate was concentrated in vacuo to obtain the product.

Yield: 0.28 g (Yield 67%)

Example 8

Production of (1S)-3-(2-cyclooctylethyl)-1,8,8-trimethyl-3-azabicyclo[3.2.1]octane:

Triethylamine 0.24 ml was added in a methylene chloride 10 ml solution of (1S)-1,8,8-trimethyl-3-azabicyclo (3.2.1] octane hydrochloride 0.28 g, and stirred at 0° C. for 30 min. Cyclooctyl acetic acid 0.25 g and WSC 0.40 g were added therein, then temperature of the reaction mixture was gradually changed to room temperature and stirred for 21 hours. The reaction mixture was washed wits saturated aqueous sodium chloride solution and dried by anhydrous sodium sulfate. After filtering the drying agent, the filtrate was concentrated in vacuo to obtain crude (1S)-3-cyclooctylacetyl-1,8,8-trimethyl-3-azabicyclo[3.2.1]octane. The concentrate was added to THP 15 ml solution of lithium aluminum hydride 0.12 g and refluxed for 1 hour. The reaction mixture was cooled, then added water and filtered the insoluble material. The filtrate was concentrated in vacuo. The thus obtained residue was purified by means of silica gel column chromatography (Wako gel, C200, chloroform: acetone=10:1) to obtain the product. Yield: 0.26 g (Yield 61%)

The product was treated by the same way as of in Example 1 to obtain the hydrochloride.

$[\alpha]_D^{25}=-12.9°$ (c=0.5, methanol)

Example 9

Production of (1S)-3-(4-cyclohexyl-1-butyl)-1,8,8-trimethyl-3-azabicyclo[3.2.1]octane:

4-cyclohexyl-1-butanol 0.52 ml was dissolved in methylene chloride 20 ml and cooled to 0° C., then methanesulfonyl chloride 0.28 ml and triethylamine 0.50 ml were added thereto. Temperature of the reaction mixture was gradually changed to room temperature and stirred for 6.5 hours. The reaction mixture was concentrated in vacuo to obtain the crude mesylate. (1S)-1,8,8-trimethyl-3-azabicyclo[3.2.1]octane hydrochloride, 0.47 g and potassium carbonate 1.04 g were added thereto, then prepared acetonitrile 20 ml solution. The solution was refluxed under heating for 15 hours. Insoluble material was removed by filtration and the filtrate was concentrated in vacuo. The thus obtained residue was purified by means of flash column chromatography (Merck, silica gel 60 230–600 mesh, chloroform) to obtain the product.

Yield: 0.55 g (Yield 75%)

The product was treated by the same way as of in Example 1 to obtain the hydrochloride.

$[\alpha]_D^{25}=-13.1°$ (c=0.5, methanol)

Example 10

Production of (1S)-3-(3-cyclohexylpropyl)-1,8,8-trimethyl-3-azabicyclo[3-2-1]octane:

Triethylamine 0.43 ml was added in a methylene chloride 20 ml solution of (1S)-1,8,8-trimethyl-3-azabicyclo[3.2.1] octane hydrochloride 0.49 g, and stirred at 0° C. for 40 min. 3-cyclohexyl propionic acid 0.44 ml and WSC 0.59 g were added therein, then temperature of the reaction mixture was gradually changed to room temperature and stirred for 45 hours. The reaction mixture was concentrated in vacuo and the residue was dissolved in ether. The ether solution was washed with 10% sodium hydroxide solution and dried by anhydrous sodium sulfate. After filtering the drying agent, the filtrate was concentrated in vacuo to obtain crude (1S)-3(3-cyclohexylpropionyl)-1,8,8-trimethyl-3-azabicyclo[3.2.1]octane. The concentrate was added to THF 20 ml solution of lithium aluminum hydride 0.19 g and refluxed for 1.5 hour. The reaction mixture was cooled, then added ether, water and 10% sodium hydroxide solution, and filtered the insoluble material. The filtrate was extracted with ether and dried by anhydrous sodium sulfate. After removing the drying agent, the filtrate was concentrated in vacuo. The thus obtained residue was purified by means of flash column chromatography (Merck, silica gel 60 230–600 mesh, chloroform-chloroform: acetone=20:1) to obtain the product.

Yield: 0.56 g (Yield 79%)

The product was treated by the same way as of in Example 1 to obtain the hydrochloride.

$[\alpha]_D^{25} = -11.3°$ (c=0.5, methanol)

Example 11

Production of (IS)-3-cyclohexylmethyl-1,8,8-trimethyl-3-azabicyclo-[3.2.1]octane:

(1S)-1,8,8-trimethyl-3-azabicyclo-[3.2.1]octane hydrochloride 0.50 g and cyclohexylmethyl bromide 0.44 ml were dissolved in acetonitrile 25 ml, added potassium carbonate 1.10 g thereto and refluxed under heating for 26 hours. Insoluble material was removed from the reaction mixture by filtration and the filtrate was concentrated in vacuo. The thus obtained residue was purified by means of flash column chromatography (Merck, silica gel 60: 230–600 mesh, chloroform-chloroform: acetone=20:1) to obtain the product.

Yield: 0.66 g (Yield 100%)

The product was treated by the same way as of in Example 1 to obtain the hydrochloride.

$[\alpha]_D^{25} = -11.0°$ (c=0.5, methanol)

Example 12

Production of (1R)-3-cyclohexylmethyl-1,8,8-trimethyl-3-azabicyclo-[3.2.1]octane:

(1R)-1,8,8-trimethyl-3-azabicyclo[3.2.1]octane 3.00 g and cyclohexylmethyl bromide 5.48 ml were dissolved in acetonitrile 50 ml, added potassium carbonate 6.78 g thereto and refluxed under heating for 39 hours. Insoluble material was removed from the reaction mixture by filtration and the filtrate was concentrated in vacuo. The thus obtained residue was purified by means of silica gel column chromatography (Wako gel, C200, chloroform) to obtain the product.

Yield: 4.62 g (Yield 95%)

The product was treated by the same way as of in Example 1 to obtain the hydrochloride.

$[\alpha]_D^{25} = -13.0°$ (c=0.5, methanol)

Example 13

Production of (1S)-3-cyclohexyl-1,8,8-trimethyl-3-azabicyclo[3.2.1]octane:

(1S)-1,8,8-trimethyl-3-azabicyclo[3.2.1]octane hydrochloride 0.12 g and cyclohexyl bromide 0.092 ml were dissolved in acetonitrile 5 ml, added potassium carbonate 0.26 g thereto and refluxed under heating for 51 hours. Insoluble material was removed from the reaction mixture by filtration and the filtrate was concentrated in vacuo. The thus obtained residue was purified by means of flash column chromatography (Merck, silica gel 60 230–600 mesh, chloroform-chloroform:acetone=20:1) to obtain the product.

Yield: 32.0 mg (Yield 22%)

The product was treated by the same way as of in Example 1 to obtain the hydrochloride.

Example 14

Production of (1R)-3-[2-(I-adamantyl)ethyl]-1,8,8-trimethyl-3-azabicyclo[3.2.1]octane:

(IR)-1,8,8-trimethyl-3-azabicyclo[3.2.1]octane hydrochloride 0.95 g (5.0 mill) and 1-adamantyl acetic acid 1. 17 g (6.0 MM) were treated by the same method as of the compound in Example I and the resulted compound was purified by means of silica gel column chromatography (Wako gel, C200, chloroform acetone=20:1) to obtain the product.

Yield: 1.21 g (Yield 77%)

The product was treated by the same way as of in Example 1 to obtain the hydrochloride.

$[\alpha]_D^2 = +9.2°$ (c=0.5, methanol)

Referential Example 8

Production of methyl 2-adamantylidene acetate:

Methanol 500 ml solution of 2-adamantanone 115.00 g (0.77 mole) and methyl diethylphosphonoacetate 210.78 ml (1.15 mole) was cooled to 0° C., and 28% methanol solution 371.7 g of sodium methylate was added dropwise. Temperature of the reaction mixture was gradually changed to room temperature and stirred for 4 hours. The reaction mixture was concentrated in vacuo and water was added to the thus obtained residue, then extracted with ethyl acetate, and dried by anhydrous sodium sulfate. The drying agent was removed by filtration and the filtrate was concentrated in vacuo. The thus obtained residue was purified by means of silica gel column chromatography (Wako gel, C200, n-hexane:ethyl acetate =20:1) to obtain the product.

Yield: 157.70 g (Yield 100%)

Referential Example 9

Production of 2-adamantyl acetic acid methyl ester:

10% Pd-C 2.90 g and ammonium formate 178 g (2.8 mole) were added to methanol 1150 ml solution of methyl 2-adamantylidene acetate 145 g (0.74 mole) and stirred at room temperature for 3 hours. Pd-C was filtered and the filtrate was concentrated in vacuo. Water was added to the thus obtained residue, extracted with ethyl acetate and dried by anhydrous sodium sulfate. The drying agent was removed by filtration and the filtrate was concentrated in vacuo to obtain the product.

Yield: 146.41 g (Yield 100%)

Referential Example 10

Production of 2-adamantyl acetic acid:

2.5N sodium hydroxide 433 ml was added to methanol 1125 ml solution of 2-adamantyl acetic acid methyl ester 150 g (0.72 mole) and stirred at room temperature for 6 hours. The reaction mixture was concentrated in vacuo, and aqueous sodium bicarbonate was added to the residue and the mixture was washed with ether. Aqueous layer was adjusted to pH I by adding 12N hydrochloric acid and extracted with ethylacetate. The extract was dried by anhydrous sodium sulfate. After removing the drying agent by filtration, the filtrate was concentrated in vacuo to obtain the product.

Yield: 129.39 g (Yield 93%)

Example 15

Production of (IS)-3-[2-(2-adamantyl)ethyl]-1,8,8-trimethyl-3-azabicyclo[3.2.1]octane:

Triethylamine 0.69 ml was added in a methylene chloride 20 ml solution of (1S)-1,8,8-trimethyl-3-azabicyclo[3.2.1]octane hydrochloride 0.78 g (4.1 mill), and stirred at 0° C.

for 30 min. 2-adamantyl acetic acid 0.80 g (4.1 mill) and WSC 1.11 g (5.79 mill) were added therein, then temperature of the reaction mixture was gradually changed to room temperature and stirred for 23 hours. The reaction mixture was washed with saturated aqueous sodium chloride solution and dried by anhydrous sodium sulfate. After filtering the drying agent, the filtrate was concentrated in vacuo to obtain crude (1S)-3-(2-adamantylacetyl)-1,8,8-trimethyl-3-azabicyclo[3.2.1]octane. The concentrate was added to THF 50 ml solution of lithium aluminum hydride 0.47 g (12 mill) and refluxed for 2 hours. The reaction mixture was cooled, added water and filtered the insoluble material. The filtrate was concentrated in vacuo. The thus obtained residue was purified by means of silica gel column chromatography (Wako gel, C200, chloroform:acetone=10:1–5:1) to obtain the product.

Yield: 1.26 g (Yield 97%)

The product was treated by the same way as of in Example 1 to obtain the hydrochloride.

$[\alpha]_D^{25} = -10.2°$ (c=0.5, methanol)

Example 16

Production of (1R)-3-[2-(2-adamantyl)ethyl]-1,8,8-trimethyl-3-azabicyclo[3.2.1]octane:

(1R)-1,8,8-trimethyl-3-azabicyclo[3.2.1]octane hydrochloride 0.38 g (2.0 mill) and 2-adamantyl acetic acid 0.43 g (2—2 mill) were treated by the same method as of the compound in Example 15 and he resulted compound was purified by means of silica gel column chromatography (Wako gel, C200, chloroform:acetone=10:1) to obtain the product.

Yield: 0.57 g (Yield 91%)

The product was treated by the same way as of in Example 1 to obtain the hydrochloride.

$[\alpha]_D^{25} = +10.5°$ (c=0.5, methanol)

Referential Example 11

Production of 2-adamantyl ethanol:

2-adamantyl acetic acid methyl ester 0.57 g (2.47 mill) was added to diethyl ether 20 ml solution of lithium aluminum hydride 0.16 g (4.2 mkf), and the reaction mixture was refluxed under heating for 2 hours. The reaction mixture was cooled and added water. Insoluble material was filtered and the filtrate was extracted with ether, then dried by anhydrous sodium sulfate, which was thereafter removed by filtration. The filtrate was concentrated in vacuo to obtain the product.

Yield: 0.23 g (Yield 47%)

Example 17

Production of (1S)-3-[2-(2-adamantyl)ethyl]-1,8,8-trimethyl-3-azabicyclo[3.2.1]octane:

Methylene chloride 10 ml solution of 2-adamantyl ethanol 0.64 g (3.6 mill) was cooled to 0° C., then methanesulfonyl chloride 0.42 ml (5.4 mill) and triethylamine 1.00 ml (7.17 mill) were added thereto. Temperature of the reaction mixture was gradually changed to room temperature and stirred for 15 hours. The reaction mixture was concentrated in vacuo to obtain the crude mesylate-(1S)-1,8,8-trimethyl-3-azabicyclo[3-2-1]octane hydrochloride 0.68 g (3.6 mill) and potassium carbonate 1.49 g (10.8 mill) were added thereto, then prepared acetonitrile 30 ml solution. The solution was refluxed under heating for 18 hours. Insoluble material was removed by filtration and the filtrate was concentrated in vacuo. The thus obtained residue was purified by means of silica gel column chromatography (Wako gel, C200, chloroform:acetone=20:1–5:1) to obtain the product.

Yield: 0.59 g (Yield 53%)

The product was treated by the same way as of in Example 1 to obtain the hydrochloride.

Example 18

Production of (1S)-3-[2-(4-methylcyclohexyl)ethyl]-1,8,8-trimethyl-3-azabicyclo[3.2.1]octane:

Triethylamine 0.84 ml was added in a methylene chloride 20 ml solution of (1S)-1,8,8-trimethyl-3-azabicyclo[3.2.1]octane hydrochloride 0.95 g, and stirred at 0° C. for 30 min. 4-methylcyclohexyl acetic acid 0.94 g and WSC 1.35 g were added therein, then temperature of the reaction mixture was gradually changed to room temperature and stirred for 24 hours. The reaction mixture was washed with saturated sodium chloride solution and dried by anhydrous sodium sulfate. After filtering the drying agent, the filtrate was concentrated in vacuo to obtain crude (1S)-3-(4-methylcyclohexylacetyl)-1,8,8-trimethyl-3-azabicyclo[3.2.1]octane. The concentrate was added to THF 30 ml solution of lithium aluminum hydride 0.39 g and refluxed for 1 hour. The reaction mixture was cooled, then added water, and filtered the insoluble material. The filtrate was concentrated in vacuo. The thus obtained residue was purified by means of silica gel column chromatography (Wako gel, C200, chloroform:acetone=10:1) to obtain the product.

Yield: 1.37 g (Yield 100%)

The product was treated by the same way as of in Example 1 to obtain the hydrochloride.

$[\alpha]_D^{25} = -11.0°$ (c=0.5, methanol)

Example 19

Production of (1S)-3-[2-(3-methyl-1-adamantyl)ethyl]-1,8,8-trimethyl-3-azabicyclo[3.2.1]octane:

Triethylamine 0.53 ml was added in a methylene chloride 15 ml solution of (1S)-1,8,8-trimethyl-3-azabicyclo[3.2.1]octane hydrochloride 0.51 g, and stirred at 0° C. for 30 min. 3-methyl-1-adamantyl acetic acid 0.68 g and WSC 0.73 g were added therein, then temperature of the reaction mixture was gradually changed to room temperature and stirred for 23.5 hours. The reaction mixture was washed with saturated aqueous sodium chloride and dried by anhydrous sodium sulfate. After filtering the drying agent, the filtrate was concentrated in vacuo to obtain crude (1S)-3-(3-methyl-1-adamantylacetyl)-1,8,8-trimethyl-3-azabicyclo[3.2.1]octane. The concentrate was added to THF 15 ml solution of lithium aluminum hydride 0.21 g and refluxed under heating for 3 hours. The reaction mixture was cooled, then added water thereto, and removed the insoluble material by filtration. The filtrate was concentrated in vacuo. The thus obtained residue was purified by means of flash column chromatography (Merck,silica gel 60: 230–600 mesh, chloroform) to obtain the product. Yield: 0.63 g (Yield 71%)

The product was treated by the same method as of in Example 1 to obtain the hydrochloride.

$[\alpha]_D^{25} = -9.4°$ (c=0.5, methanol)

Example 20

Production of (1S)-3-(3-noradamantylmethyl)-1,8,8-trimethyl-3-azabicyclo[3.2.1]octane:

Triethylamine 0.096 ml was added in a methylene chloride 5 ml solution of (1S-)-1,8,8-trimethyl-3-azabicyclo[3.2.1]octane hydrochloride 100 mg, and stirred at 0° C. for 30 min. WSC 0.132 g and 3-noradamantanecarboxylic acid 96.5 mg were added therein, then temperature of the reaction mixture was gradually changed to room temperature and stirred for 15.5 hours. The reaction mixture was washed with saturated sodium chloride solution and dried by anhydrous sodium sulfate. After filtering the drying agent, the filtrate was concentrated in vacuo to obtain crude (1S)-3-(3-noradamantylcarbonyl)-1,8,8-trimethyl-3-azabicyclo[3.2.1]octane. The concentrate was added to THF 10 ml solution of lithium aluminum hydride 24.0 mg and refluxed under heating for 1.5 hours. The reaction mixture was cooled, then added water, and removed the insoluble material by filtration. The filtrate was concentrated in vacuo. The thus obtained residue was purified by means of silica gel column chromatography (Wako gel, C200, chloroform) to obtain the product.

Yield: 118.2 mg (Yield 78%)

The product was treated by the same way as of in Example 1 to obtain the hydrochloride.

$[\alpha]_D^{25} = -9.4°$ (c=0.5, methanol)

Referential Example 12

Production of methyl 9-bicyclo[3.3.1]nonylidene acetate:

Sodium hydride (60%, oil dispersion) 0.30 g was added to 1,2-dimethoxyethane (DME) 10 ml solution of bicyclo [3.3.1]nonan-9-one 0.50 g and methyl diethylphosphonoacetate 1.00 ml and stirred at room temperature for 3 hours. Water was added to the reaction mixture to decompose unreacted sodium hydride, and DME was concentrate in vacuo. The residue was extracted with chloroform and dried by anhydrous sodium sulfate. After removing the drying agent, the filtrate was concentrated. The residue was purified by means of silica gel column chromatography (Wako gel, C200, n-hexane:ethyl acetate=20:1) to obtain the product.
Yield: 0.70 g (Yield 100%)

Referential Example 13

Production of 9-bicyclo[3.3.1]nonylacetic acid methyl ester:

10% Pd-C 0.07 g was added in a methanol solution 10 ml of methyl 9-bicyclo[3.3.1]nonylidene acetate 0.70 g, and the reaction mixture was subjected to catalytic hydrogenation under hydrogen atmosphere at normal temperature and normal pressure for 2 hours. Pd-C was removed from the reaction mixture by filtration and the filtrate was concentrated in vacuo to obtain the product.

Yield: 0.67 g (Yield 94%)

Referential Example 14

Production of 9-bicyclo[3.3.1]nonylacetic acid:

1N aqueous sodium hydroxide 5.2 ml was added to methanol 15 ml solution of 9-bicyclo[3.3.1]nonylacetic acid methyl ester 0.67 g and stirred at room temperature for 5 hours. The reaction mixture was concentrated in vacuo, and saturated aqueous sodium bicarbonate was added to the residue and the mixture was washed with ether. Aqueous layer was adjusted to pH 1 by adding 12N hydrochloric acid and extracted with ethyl acetate. The extract was dried by anhydrous sodium sulfate. After removing the drying agent by filtration, the filtrate was concentrated in vacuo to obtain the product.

Yield: 0.44 g (Yield 71%)

Example 21

Production of (1S)-3-[2-(bicyclo[3.3.1]nonan-9-yl)-ethyl]-1,8,8-trimethyl-3-azabicyclo (3.2.1)octane:

Triethylamine 0.12 ml was added in a methylene chloride 10 ml solution of (1S)-1,8,8-trimethyl-3-azabicyclo[3.2.1]octane hydrochloride 100 mg and stirred at 0° C. for 30 min. 9-bicyclo[3.3.1]nonylacetic acid 97.0 mg and WSC 0.15 g were added therein, then temperature of the reaction mixture was gradually changed to room temperature and stirred for 19 hours. The reaction mixture was washed with saturated aqueous sodium chloride solution and dried by anhydrous sodium sulfate. After filtering the drying agent, the filtrate was concentrated in vacuo to obtain crude (1S)-3-(bicyclo [3.3.1]nonan-9-yl)acetyl-1,8,8-trimethyl-3-azabicyclo [3.2.1]octane. The concentrate was added to THF 10 ml solution of lithium aluminum hydride 41 mg and refluxed under heating for 1 hour. The reaction mixture was cooled, then water was added thereto and the insoluble material was removed by filtration. The filtrate was concentrated in vacuo. The thus obtained residue was purified by means of silica gel column chromatography (Wako gel, C200, chloroform:acetone=10:1–5:1) to obtain the product.

Yield: 110 mg (Yield 69%)

The product was treated by the same way as of in Example 1 to obtain the hydrochloride.

$[\alpha]_D^{25} = -17.9°$ (c=0.5, methanol)

Example 22

Production of (1S)-3-(I-adamantylmethyl)-1,8,8-trimethyl-3-azabicyclo[3.2.1]octane:

Triethylamine 0.096 ml was added in a methylene chloride 5 ml solution of (IS)-1,8,8-trimethyl-3-azabicyclo [3.2.1]octane hydrochloride 100 mg, and stirred at 0° C. for 30 min. WSC 0.13 g and 1-adamantanecarboxylic acid 0.11 g were added therein, then temperature of the reaction mixture was gradually changed to room temperature and stirred for 15 hours. The reaction mixture was washed with saturated sodium chloride solution and dried by anhydrous sodium sulfate. After filtering the drying agent, the filtrate was concentrated in vacuo to obtain crude (IS)-3-(1-adamantyl carbonyl)-1,8,8-trimethyl-3-azabicyclo[3.2.1] octane. The concentrate was added to THF 10 ml solution of lithium aluminum hydride 24.0 mg and refluxed under heating for 1.5 hour. The reaction mixture was cooled, then added water, and removed the insoluble material by filtration. The filtrate was concentrated in vacuo. The thus obtained residue was purified by means of silica gel column chromatography (Wako gel, C200, chloroform) to obtain the product.

Yield: 71.2 mg (Yield 45%)

The product was treated by the same way as of in Example 1 to obtain the hydrochloride.

$[\alpha]_D^{25} = -10.5°$ (c=0.5, methanol)

Referential Example 15

Production of methyl 5-hydroxy-2-adamantylidene acetate:

DME 5 ml solution of methyl diethylphosphonoacetate 0.200 ml was cooled to −10° C. Sodium hydride (60%, oil dispersion) 54.3 mg was added thereto and stirred at the same temperature for I hour. DME 5 ml solution of 5-hydroxy-2-adamantanone 150 mg was added thereto and stirred at the same temperature for 1.5 hours. Water was added to the reaction mixture and DME was concentrated in vacuo. The residue was extracted with chloroform and dried by anhydrous sodium sulfate. After removing the drying agent, the filtrate was concentrated. The residue was purified by means of silica gel column chromatography (Wako gel, C200, chloroform) to obtain the product.

Yield: 180 mg (Yield 90%)

Referential Example 16

Production of 5-hydroxy-2-adamantylacetic acid methyl ester:

10% Pd-C 18.0 mg was added to a methanol solution 5 ml of methyl 5-hydroxy-2-adamantylidene acetate 179.9 mg, and the reaction mixture was subjected to catalytic hydrogenation under hydrogen atmosphere at normal temperature and normal pressure for 2.5 hours. Pd-C was removed from the reaction mixture by filtration and the filtrate was concentrated in vacuo to obtain the colorless oily product.

Yield: 166.3 mg (Yield 92%)

The compound obtained was a mixture of the stereoisomer (mixture of 1:1 measured by gas chromatography).

Referential Example 17

Production of 5-hydroxy-2-adamantylacetic acid:

2.5N aqueous sodium hydroxide 0.49 ml was added to methanol 10 ml solution of 5-hydroxy-2-adamantylacetic acid methyl ester 181.5 mg and stirred at room temperature for 14 hours. The reaction mixture was concentrated in vacuo, and aqueous sodium bicarbonate was added to the residue and the mixture was washed with ether. Aqueous layer was adjusted to PH 1 by adding 12N hydrochloric acid and extracted with ethyl acetate. The extract was dried by anhydrous sodium sulfate. After removing the drying agent by filtration, the filtrate was concentrated in vacuo to obtain the product. Yield: 150 mg (Yield 88%)

The compound obtained was a mixture of the stereoisomer (mixture of 1:1 measured by gas chromatography).

Example 23

Production of (1S)-3-[2-(5-hydroxy-2-adamantyl)ethyl]-1,8,8-trimethyl-3-azabicyclo[3.2.1]octane:

Triethylamine 0.38 ml was added to a methylene chloride 15 ml solution of (1S)-1,8,8-trimethyl-3-azabicyclo[3.2.1] octane hydrochloride 0.44 g, and stirred at 0° C. for 30 min. WSC 0.53 g and 5-hydroxy-2-adamantyl acetic acid 0.44 g were added therein, then temperature of the reaction mixture was gradually changed to room temperature and stirred for 14.5 hours. The reaction mixture was washed with saturated sodium chloride solution and dried by anhydrous sodium sulfate. After filtering the drying agent, the filtrate was concentrated in vacuo to obtain crude (1S)-3-(5-hydroxy-2-adamantyl acetyl)-1,8,8-trimethyl-3-azabicyclo[3.2.1]octane. The concentrate was added to THF 30 ml solution of lithium aluminum hydride 95.5 mg and refluxed under heating for 1.5 hours. The reaction mixture was cooled, then added water, and removed the insoluble material by filtration. The filtrate was concentrated in vacuo. The thus obtained residue was purified by means of silica gel column chromatography (Wako gel, C200, chloroform: methanol= 150:1) to obtain the product. Yield: 556 mg (Yield 79%)

The product was treated by the same way as of in Example 1 to obtain the hydrochloride.

The compound obtained was a mixture of the stereoisomer (mixture of 1:1 measured by gas chromatography).

$[\alpha]_D^{25}=-10.9°$ (c=0.5, methanol)

Referential Example 18

Production of 5-methoxy-2-adamantanone:

THF 5 ml solution of 5-hydroxy-2-adamantanone 100 mg and methyl iodide 0.113 ml was cooled to 0° C. Sodium hydride (60%, oil dispersion) 48.2 mg was added to thereto and temperature of the reaction mixture was gradually changed to room temperature and stirred for 25 hours. Water was added to the reaction mixture and THF was concentrated in vacuo. The thus obtained residue was extracted with chloroform and dried by anhydrous sodium sulfate. After removing the drying agent, the filtrate was concentrated in vacuo. The residue was purified by means of silica gel column chromatography (Wako gel, C200, n-hexane:ethyl acetate=10:1) to obtain the product. Yield: 57.7 mg (Yield 54%)

Referential Example 19

Production of methyl 5-methoxy adamantylidene acetate:

DME 2 ml solution of 5-methoxy-2-adamantanone 57.7 mg and methyl diethylphosphonoacetate 70.6 u I was cooled to 0° C. Sodium hydride (60 %, oil dispersion) 25.6 mg was added thereto and temperature of the reaction mixture was gradually changed to room temperature and stirred for 3.5 hours. Water was added to the reaction mixture to decompose unreacted sodium hydride and DME was concentrated in vacuo. The residue was extracted with chloroform and dried by anhydrous sodium sulfate. After removing the drying agent, the filtrate was concentrated. The residue was purified by means of silica gel column chromatography (Wako gel, C200, n-hexane:ethyl acetate=10:1) to obtain the product. Yield: 53.2 mg (Yield 70%)

Referential Example 20

Production of 5-methoxy-2-adamantyl acetic acid methyl ester: 10% Pd-C 5.3 mg was added to a methanol solution 2 ml of methyl 5-hydroxy-2-adamantylidene acetate 53.2 mg, and the reaction mixture was subjected to catalytic hydrogenation under hydrogen atmosphere at normal temperature and normal pressure for 1.5 hours. Pd-C was removed from the reaction mixture by filtration and the filtrate was concentrated in vacuo to obtain the product.

Yield: 50.0 mg (Yield 93%)

The compound obtained was a mixture of the stereoisomer (mixture of 1:1 measured by gas chromatography).

Referential Example 21

Production of 5-methoxy-2-adamantyl acetic acid:

2.5N aqueous sodium hydroxide 0.13 ml was added to methanol 2 ml solution of 5-methoxy-2-adamantyl acetic acid methyl ester 50.0 mg and stirred at room temperature for 7 hours. The reaction mixture was concentrated in vacuo, and saturated aqueous sodium bicarbonate was added to the residue and the mixture was washed with ether. Aqueous layer was adjusted to pH 1 by adding 12N hydrochloric acid and extracted with ethyl acetate. The extract was dried by anhydrous sodium sulfate. After removing the drying agent by filtration, the filtrate was concentrated in vacuo to obtain the product. Yield: 36.2 mg (Yield 77%)

The compound obtained was a mixture of the stereoisomer (mixture of 1:1 measured by gas chromatography).

Example 24

Production of (1S)-3-[2-(5-methoxy-2-adamantyl)ethyl]-1,8,8-trimethyl-3-azabicyclo[3.2.1]octane:

Triethylamine 29.3 µl was added to a methylene chloride 1 ml solution of (IS)-1,8,8-trimethyl-3-azabicyclo[3.2.1] octane hydrochloride 33.7 mg and stirred at 0° C. for 30 min. 5-methoxy-2-adamantyl acetic acid 36.2 mg and WSC 40.3 mg were added therein, then temperature of the reaction mixture was gradually changed to room temperature and stirred for 20.5 hours. The reaction mixture was washed with saturated aqueous sodium chloride solution and dried by anhydrous sodium sulfate. After filtering the drying agent, the filtrate was concentrated in vacuo to obtain crude (IS)-3-(5-methoxy-2-adamantylacetyl)-1,8,8-trimethyl-3-azabicyclo[3.2.1]octane. The concentrate was added to THF 3 ml solution of lithium aluminum hydride 7.4 mg and refluxed under heating for 1.5 hours. The reaction mixture was cooled, then water was added thereto and then insoluble material was removed by filtration. The filtrate was concentrated in vacuo. The thus obtained residue was purified by means of silica gel column chromatography (Wako gel, C200, chloroform:acetone=20:1–10:1) to obtain the product.

Yield: 32.1 mg (Yield 58%)

The product was treated by the same way as of in Example 1 to obtain the hydrochloride.

The compound obtained was a mixture of the stereoisomer (mixture 1:1 measured by gas chromatography).

$[\alpha]_D^{25} = -22.5°$ (c=0.5, methanol)

Example 25

Production of (IS)-3-[2-(5-chloro-2-adamantyl)ethyl]-1,8,8-trimethyl-3-azabicyclo[3.2.1]octane:

Thionyl chloride 5 ml was added to (IS)-3-[2-(5-hydroxy-2-adamantyl)ethyl]-1,8,8-trimethyl-3-azabicyclo[3.2.1]octane 80.3 mg and refluxed under heating for 4.5 hours. The reaction mixture was concentrated in vacuo, and the residue obtained was alkalified by adding IN sodium hydroxide, then extracted with chloroform. The extract was dried by anhydrous sodium sulfate. After the drying agent was removed by filtration, the filtrate was concentrate in vacuo. The thus obtained residue was purified by means of silica gel column chromatography (Wako gel, C200, chloroform:acetone=20:1) to obtain the product. Yield: 44.8 mg (Yield 53%)

The compound obtained was a mixture of the stereoisomer (mixture of 1:1 measured by gas chromatography).

The product was treated by the same way as of in Example 1 to obtain the hydrochloride.

$[\alpha]_D^{25} = -12.2°$ (c=0.5, methanol)

Referential Example 22

Production of methyl 5-phenyl-2-adamantylidene acetate:

DME 2 ml solution of 5-phenyl-2-adamantanone 86.1 mg and methyl diethylphosphonoacetate 84.0 gl was cooled to 0° C., and sodium hydride (60%, oil dispersion) 22.9 mg was added thereto, then stirred at 0° C. for 1.5 hours. Water was added to the reaction mixture to decompose unreacted sodium hydride, and DME was concentrated in vacuo. The residue was extracted with chloroform and dried by anhydrous sodium sulfate. After removing the drying agent, the filtrate was concentrated. The residue was purified by means of silica gel column chromatography (Wako gel, C200, n-hexane:ethyl acetate=30:1) to obtain the product. Yield: 55.3 mg (Yield 52%)

Referential Example 23

Production of 5-phenyl-2-adamantyl acetic acid methyl ester:

10% Pd-C 5.3 mg was added to a methanol solution 2 ml of methyl 5-phenyl-2-adamantylidene acetate 55.3 mg, and the reaction mixture was subjected to catalytic hydrogenation under hydrogen atmosphere at normal temperature and normal pressure for 2.5 hours. Pd-C was removed from the reaction mixture by filtration and the filtrate was concentrated in vacuo to obtain the product.

Yield: 55.7 mg (Yield 100%)

The compound obtained was a mixture of the stereoisomer (mixture of 1:1 measured by gas chromatography).

Referential Example 24

Production of 5-phenyl-2-adamantyl acetic acid:

2.5N aqueous sodium hydroxide 0.12 ml was added to methanol 3 ml solution of 5-phenyl-2-adamantyl acetic acid methyl ester 55.7 mg and stirred at room temperature for 14.5 hours. The reaction mixture was concentrated in vacuo, and saturated aqueous sodium bicarbonate was added to the residue and the mixture was washed with ether. Aqueous layer was adjusted to PH 1 by adding 12N hydrochloric acid and extracted with ethyl acetate. The extract was dried by anhydrous sodium sulfate. After removing the drying agent by filtration, the filtrate was concentrated in vacuo to obtain the product. Yield: 22.6 mg (Yield 43%)

The compound obtained was a mixture of the stereoisomer (mixture of 1:1 measured by gas chromatography).

Example 26

Production of (1S)-3-[2-(5-phenyl-2-adamantyl)ethyl]-1,8,8-trimethyl-3-azabicyclo[3.2.1]octane:

Triethylamine 14.0 gl was added to a methylene chloride 1 ml solution of (1S)-1,8,8-trimethyl-3-azabicyclo[3.2.1]octane hydrochloride 15.9 mg and stirred at O@C for 30 min. 5-phenyl-2-adamantyl acetic acid 22.6 mg and WSC 19.3 mg were added therein, then temperature of the reaction mixture was gradually changed to room temperature and stirred for 64 hours. The reaction mixture was washed with saturated aqueous sodium chloride solution and dried by anhydrous sodium sulfate. After filtering the drying agent, the filtrate was concentrated in vacuo to obtain crude (1S)-3-(5-phenyl-2-adamantylacetyl)1,8,8-trimethyl-3-azabicyclo[3.2.1]octane. The concentrate was added to THF 3 ml solution of lithium aluminum hydride 3.8 mg and refluxed under heating for 1.5 hours. The reaction mixture was cooled, then water was added thereto and the insoluble material was removed by filtration. The filtrate was concentrated in vacuo. The thus obtained residue was purified by means of silica gel column chromatography (Wako gel, C200, chloroform: acetone 20:1) to obtain the product. Yield: 7.0 mg (Yield 21%)

The compound obtained was a mixture of the stereoisomer (mixture of 1:1 measured by gas chromatography).

The product was treated by the same way as of in Example 1 to obtain the hydrochloride.

Referential Example 25

Production of methyl 4-hydroxy-2-adamantylidene acetate:

DME 20 ml solution of 4-hydroxy-2-adamantanone 536.1 mg and methyl diethylphosphonoacetate 0.72 ml was cooled to −10° C., and sodium hydride (60%, oil dispersion) 259 mg was added thereto, then stirred at −10° C. for 1.5 hours. Water was added to the reaction mixture to decompose unreacted sodium hydride, and DME was concentrate in vacuo. The residue was extracted with chloroform and dried by anhydrous sodium sulfate. After removing the drying agent, the filtrate was concentrated. The residue was purified by means of silica gel column chromatography (Wako gel, C200, chloroform) to obtain the product.

Yield: 0.51 g (Field 71%)

The compound obtained is a mixture of stereoisomer.

Referential Example 26

Production of 4-hydroxy-2-adamantyl acetic acid methyl ester:

10% Pd-C 51 mg was added to a methanol solution 20 ml of methyl 4-hydroxy-2-adamantylidene acetate 0.51 g, and the reaction mixture was subjected to catalytic hydrogenation under hydrogen atmosphere at normal temperature and normal pressure for 1 hour. Pd-C was removed from the reaction mixture by filtration and the filtrate was concentrated in vacuo to obtain the product.

Yield: 0.47 g (Yield 92%)

The compound obtained is a mixture of stereoisomer.

Referential Example 27

Production of 4-hydroxy-2-adamantyl acetic acid: 2.5N aqueous sodium hydroxide 1.26 ml was added to methanol 15 ml solution of 4-hydroxy-2-adamantyl acetic acid -methyl ester 0.47 g and stirred at room temperature for 5.5 hours. The reaction mixture was concentrated in vacuo, and saturated aqueous sodium bicarbonate was added to the residue and the mixture was washed with ether. Aqueous layer was adjusted to PH 1 by adding 12N hydrochloric acid and extracted with ethyl acetate. The extract was dried by anhydrous sodium sulfate. After removing the drying agent by filtration, the filtrate was concentrated in vacuo to obtain the product. Yield: 0.269 (Yield 59%)

The compound obtained was a mixture of stereoisomer.

Example 27

Production of (1S)-3-[2-(4-hydroxy-2-adamantyl)ethyl]-1,8,8-trimethyl-3-azabicyclo[3.2.1]octane:

Triethylamine 0.23 ml was added to a methylene chloride 5 ml solution of (IS)-1,8,8-trimethyl-3-azabicyclo[3.2.1]octane hydrochloride 0.26 g and stirred at O@C for 30 min. 4-hydroxy-2-adamantyl acetic acid 0.26 g and WSC 0.31 g were added therein, then temperature of the reaction mixture was gradually changed to room temperature and stirred for 25 hours. The reaction mixture was washed with saturated aqueous sodium chloride solution and dried by anhydrous sodium sulfate. After filtering the drying agent, the filtrate was concentrated in vacuo to obtain crude (IS)-3-(4-hydroxy-2-adamantylacetyl)1,8,8-trimethyl-3-azabicyclo[3.2.1]octane. The concentrate was added to THF 25 ml solution of lithium aluminum hydride 70.5 mg and refluxed under heating for 1.5 hours. The reaction mixture was cooled, then water was added thereto and the insoluble material was removed by filtration. The filtrate was concentrated in vacuo. The thus obtained residue was purified by means of silica gel column chromatography (Wako gel, C200, chloroform methanol=150:1) to obtain the product.

Yield: 160.5 mg (Yield 39%)

The compound obtained was a mixture of stereoisomer.

The product was treated by the same way as of in Example 1 to obtain the hydrochloride.

Referential Example 28

Production of methyl 4-phenyl-2-adamantylidene acetate:

Sodium hydride (60%, oil dispersion) 506 mg was added to DME 50 ml solution of 4-phenyl-2-adamantanone 1.43 g and methyl diethylphosphonoacetate 1.74 ml and stirred at room temperature for 23.5 hours. Ether was added to the reaction mixture and washed with water, then dried by anhydrous sodium sulfate. After removing the drying agent, the filtrate was concentrated. The residue was purified by means of flash silica gel column chromatography (Merck, silica gel 60: 230–400 mesh, n-hexane:ethyl acetate=8:1) to obtain the product.

Yield: 866 mg (Yield 49%)

The compound obtained was a mixture of stereoisomer.

Referential Example 29

Production of 4-phenyl-2-adamantyl acetic acid methyl ester:

10% Pd-C 100 mg was added in a methanol solution 15 ml of methyl 4-phenyl-2-adamantylidene acetate 838 mg, and the reaction mixture was subjected to catalytic hydrogenation under hydrogen atmosphere at normal temperature and normal pressure for I hour. Pd-C was remove from the reaction mixture by filtration and the filtrate was concentrated in vacuo to obtain the product. Yield: 838 mg (Yield 96%)

The compound obtained was a mixture of stereoisomer.

Referential Example 30

Production of 4-phenyl-2-adamantyl acetic acid:

1N aqueous-sodium hydroxide 6 ml was added to methanol 20 ml solution of 4-phenyl-2-adamantyl acetic acid methyl ester 838 mg and stirred at room temperature for 1–3.5 hours. The reaction mixture was concentrated in vacuo, and saturated aqueous sodium bicarbonate was added to the residue and the mixture was washed with ether. Aqueous layer was adjusted to PH 1 by adding 12N hydrochloric acid and extracted with methylene chloride. The extract was dried by anhydrous sodium sulfate. After removing the drying agent by filtration, the filtrate was concentrated in vacuo to obtain the product.

Yield: 774 mg (Yield 97%)

The compound obtained was a mixture of stereoisomer.

Example 28

Production of (IS)-3-[2-(4-phenyl-2-adamantyl)ethyl]-1,8,8-trimethyl-3-azabicyclo[3.2.1]octane:

Triethylamine 1.00 ml was added in a methylene chloride 30 ml solution of (1S)-1,8,8-trimethyl-3-azabicyclo[3.2.1]octane hydrochloride 815 mg, and stirred at 0° C. for 30 min. 4-phenyl-2-adamantyl acetic acid 774 mg and WSC 1.65 g were added therein, then temperature of the reaction mixture was gradually changed to room temperature and stirred for 16.5 hours. The reaction mixture was washed with 1N hydrochloric acid and dried by anhydrous sodium sulfate. After filtering the drying agent, the filtrate was concentrated in vacuo to obtain crude (IS)-3-(4-phenyl-2-adamantylacetyl)1,8,8-trimethyl-3-azabicyclo[3.2.1]octane. The concentrate was added to THF 30 ml solution of lithium aluminum hydride 229 mg and refluxed under heating for I hour. The reaction mixture was cooled, then added water and 2.5N sodium hydroxide thereto, and removed the insoluble material by filtration. The filtrate was concentrated in vacuo. The thus obtained residue was purified by means of flash column chromatography (Merck, silica gel 60: 230–400 mesh, chloroform) to obtain the product. Yield: 878 mg (Yield 78%)

The compound obtained was a mixture of stereoisomer.

The product was treated by the same method as of in Example 1 to obtain the hydrochloride.

$[\alpha]_D^{25}=-8.9°$ (c=0.5, methanol)

Example 29

Production of (IR)-3-[2-(4-phenyl-2-adamantyl)ethyl]-1,8,8-trimethyl-3-azabicyclo[3.2.1]octane:

Example 28 was repeated except that (1R)-1,8,8-trimethyl-3-azabicyclo[3.2.1]octane hydrochloride 0.48 g and 4-phenyl-2-adamantyl acetic acid 0.59 g were used and purification was performed by silica gel column chromatography (Wako gel, C200, chloroform), and the other processes were taken almost same way as of in Example 28 to obtain the product.

Yield: 0.69 g (Yield 82%)

The compound obtained was a mixture of stereoisomer.

The product was treated by the same method as of in Example 1 to obtain the hydrochloride. $[\alpha]_D^{25}=-11.8°$ (c=0.5, methanol)

Example 30

Production of (IR)-3-[2-(5-methoxy-2-adamantyl)ethyl]-1,8,8trimethyl-3-azabicyclo[3.2.1]octane:

Example 24 was repeated except that (1R)-1,8,8-trimethyl-3-azabicyclo[3.2.1]octane hydrochloride 28.4 mg and 5-methoxy-2-adamantyl acetic acid 36.9 mg were used and purification was performed by silica gel column chromatography (Wako gel, C200, chloroform:acetone=10:1), and the other processes were taken almost same way as of in Example 24 to obtain the product. Yield: 34.1 mg (Yield 66%)

The compound obtained was a mixture of the stereoisomer (mixture of I:I measured by gas chromatography).

The product was treated by the same method as of in Example 1 to obtain the hydrochloride. $[\alpha]_D^{25}=-18.7°$ (c=0.5, methanol)

Example 31

Production of (IR)-3-[2-(5-hydroxy-2-adamantyl)ethyl]-1,8,8-trimethyl-3-azabicyclo[3.2.1]octane:

Example 23 was repeated except that (1R)-1,8,8-trimethyl-3-azabicyclo[3.2.1]octane hydrochloride 0.15 g and 5-hydroxy-2-adamantyl acetic acid 0.15 g were used and purification was performed by silica gel column chromatography (Wako gel, C200, chloroform:methanol=100 1), and the other processes were taken almost same way as of in Example 23 to obtain the product. Yield: 0.16 g (Yield 66%)

The compound obtained was a mixture of the stereoisomer (mixture of 1:1 measured by gas chromatography)

The product was treated by the same method as of in Example 1 to obtain the hydrochloride. $[\alpha]_D^{25}=+11.2°$ (c=0.5, methanol)

Example 32

Production of (IR)-3-[2-(5-chloro-2-adamantyl)ethyl]-1,8,8-trimethyl-3-azabicyclo[3.2.1]octane:

Thionyl chloride 5 ml was added to (1R)-3-[2-(5-hydroxy-2-adamantyl) ethyl]-1,8,8-trimethyl-3-azabicyclo[3.2.1]octane 82.8 mg and reflexed under heating for 5 hours. The reaction mixture was concentrated in vacuo, and the residue obtained was alkalified by adding 1N sodium hydroxide, then extracted with chloroform. The extract was dried by anhydrous sodium sulfate. After the drying agent was removed by filtration, the filtrate was concentrated in vacuo. The thus obtained residue was purified by means of silica gel column chromatography (Wako gel, C200, chloroform:acetone 20:1) to obtain the product. Yield: 48.1 mg (Yield 55%)

The compound obtained was a mixture of the stereoisomer (mixture of 1:1 measured by gas chromatography).

The product was treated by the same method as of in Example 1 to obtain the hydrochloride.

$[\alpha]_D^{25}=+13.6°$ (c=0.5, methanol)

Example 33

Production of (IR)-3-[2-(5-phenyl-2-adamantyl)ethyl]-1,8,8-trimethyl-3-azabicyclo[3.2-1]octane:

Example 26 was repeated except that (IR)-1,8,8-trimethyl-3-azabicyclo[3.2.1]octane hydrochloride 37.2 mg and 5-phenyl-2-adamantyl acetic acid 53.0 mg were used and purification was performed by silica gel column chromatography (Wako gel, C200, chloroform:acetone=20:1), and the other processes were taken almost same way as of in Example 26 to obtain the product. Yield: 11.0 mg (Yield 13%)

The compound obtained was a mixture of the stereoisomer (mixture of I:1 measured by gas chromatography).

The product was treated by the same method as of in Example 1 to obtain the hydrochloride.

Example 34

Production of (IR)-3-[2-(4-hydroxy-2-adamantyl)ethyl]-1,8,8trimethyl-3-azabicyclo[3.2.1]octane:

Example 27 was repeated except that (1R)-1,8,8-trimethyl-3-azabicyclo[3.2.1]octane hydrochloride 0.22 g and 4-hydroxy-2-adamantyl acetic acid 0.37 g were used and purification was performed by silica gel column chromatography (Wako gel, C200, chloroform:methanol= 150:1), and the other processes were taken almost same way as of in Example 27 to obtain the product. Yield: 74 mg (Yield 19%)

The compound obtained was a mixture of the stereoisomer.

The product was treated by the same method as of in Example 1 to obtain the hydrochloride.

Example 35

Production of (1R)-3-[2-(3-methyl-1-adamantyl)ethyl]-1,8,8-trimethyl-3-azabicyclo[3.2.1]octane:

Example 19 was repeated except that (1R)-1,8,8-trimethyl-3-azabicyclo[3.2.1]octane hydrochloride 0.50 g and 3-methyl-1-adamantyl acetic acid 0.65 g were used and purification was performed by silica gel column chromatography (Wako gel, C200, chloroform), and the other processes were taken almost same way as of in Example 19 to obtain the product.

Yield: 0.74 g (Yield 85%)

The product was treated by the same method as of in Example 1 to obtain the hydrochloride.

$[\alpha]_D^{25}=+10.6°$ (c=0.5, methanol)

Example 36

Production of (1S)-3-[3-(2-adamantyl)-1-propyl-1,8,8-trimethyl-3-azabicyclo[3.2.1]octane:

Triethylamine 44.1 µl was added to a methylene chloride of (1S)-1,8,8-trimethyl-3-azabicyclo[3.2.1]octane hydrochloride 50.0 mg and stirred at 0° C. for 30 min. 3-(2-adamantyl) propionic acid 60.4 mg and WSC 65.7 mg were added therein, then temperature of the reaction mixture was gradually changed to room temperature and stirred for 13 hours. The reaction mixture was washed with saturated aqueous sodium chloride solution and dried by anhydrous sodium sulfate. After filtering the drying agent, the filtrate was concentrated in vacuo to obtain crude (IS)-3-[3-(2-adamantyl)propionyl]-1,8,8-trimethyl-3-azabicyclo[3.2.1]octane. The concentrate was added to THF 5 ml solution of lithium aluminum hydride 12.0 mg and refluxed under heating for 3 hours. The reaction mixture was cooled, then water was added thereto and the insoluble material was removed by filtration. The filtrate was concentrated in vacuo. The thus obtained residue was purified by means of, silica gel column chromatography (Wako gel, C200, chloroform) to obtain the product.

Yield: 61.6 mg (Yield 71%)

The product was treated by the same way as of in Example 1 to obtain the hydrochloride.

$[\alpha]_D^{25} = -9.8°$ (c=0.5, methanol)

Example 37

Production of (IR)-3-[3-(2-adamantyl)-1-propyl-1,8,8-trimethyl-3-azabicyclo[3.2.1]octane:

Example 36 was repeated except that (IR)-1,8,8-trimethyl-3-azabicyclo[3.2.1]octane hydrochloride 50.0 mg and 3-(2-adamantyl) propionic acid 60.4 mg were used and purification was performed by silica gel column chromatography (Wako gel, C200, chloroform), and the other processes were taken almost same way as of in Example 36 to obtain the product. Yield: 59.0 mg (Yield 68%)

The product was treated by the same method as of in Example 1 to obtain the hydrochloride.

$[\alpha]_D^{25} = +9.6°$ (c=0.5, methanol)

Example 38

Production of (IS)-3-[2-(3-noradamantyl)ethyl]-1,8,8-trimethyl-3-azabicyclo[3.2.1]octane:

Triethylamine 44.1 μl was added to a methylene chloride 3 ml solution of (1S)-1,8,8-trimethyl3-azabicyclo[3.2.1]octane hydrochloride 50.0 mg, and stirred at 0° C. for 30 min. WSC 65.7 mg and 3-noradamantyl acetic acid 52.2 mg were added therein, then temperature of the reaction mixture was gradually changed to room temperature and stirred for 18 hours. The reaction mixture was washed with saturated sodium chloride solution and dried by anhydrous sodium sulfate. After filtering the drying agent, the filtrate was concentrated in vacuo to obtain crude (1S)-3-(3-noradamantylacetyl)-1,8,8-trimethyl-3-azabicyclo[3.2.1]octane. The concentrate was added to THF 5 ml solution of lithium aluminum hydride 12.0 mg and refluxed under heating for 3 hours. The reaction mixture was cooled, then added water, and removed the insoluble material by filtration. The filtrate was concentrated in vacuo. The thus obtained residue was purified by means of silica gel column chromatography (Wako gel, C200, chloroform) to obtain the product.

Yield: 65. gmg (Yield 83%)

The product was treated by the same way as of in Example 1 to obtain the hydrochloride.

$[\alpha]_D^{25} = -9.8°$ (c=0.5, methanol)

Example 39

Production of (IS)-3-(2-adamantylmethyl)-1,8,8-trimethyl-3-azabicyclo[3.2.1]octane:

Triethylamine 0.096 ml was added to a methylene chloride 5 ml solution of (1S)-1,8,8-trimethyl-3-azabicyclo[3.2.1]octane hydrochloride 100 mg and stirred at O@C for 30 min. 2-adamantane carboxylic acid 0.11 g and WSC 0.13 g were added therein, then temperature of the reaction mixture was gradually changed to room temperature and stirred for 17 hours. The reaction mixture was washed with saturated aqueous sodium chloride solution and dried by anhydrous sodium sulfate. After filtering the drying agent, the filtrate was concentrated in vacuo to obtain crude (1S)-3-(2-adamantylcarbonyl)-1,8,8-trimethyl-3-azabicyclo[3.2.1]octane. The concentrate was added to THF 10 ml solution of lithium aluminum hydride 24.0 mg and refluxed under heating for 2 hours. The-reaction mixture was cooled, then water was added thereto and the insoluble material was removed by filtration. The filtrate was concentrated in vacuo. The thus obtained residue was purified by means of silica gel column chromatography (Wako gel, C200, chloroform) to obtain the product.

Yield: 53.0 mg (Yield 33%)

The product was treated by the same way as of in Example 1 to obtain the hydrochloride.

$[\alpha]_D^{25} = -9.7°$ (c=0.5, methanol)

Example 40

Production of (IR)-3-(2-adamantylmethyl)-1,8,8-trimethyl-3-azabicyclo[3.2.1]octane:

Example 39 was repeated except that (IR)-1,8,8-trimethyl-3-azabicyclo[3.2.1]octane hydrochloride 100 mg and 2-adamantane carboxylic acid O.IIg were used and purification was performed by silica gel column chromatography (Wako gel, C200, chloroform), and the other processes were taken almost same way as of in Example 39 to obtain the product.

Yield: 55.2 mg (Yield 34%)

The product was treated by the same method as of in Example 1 to obtain the hydrochloride.

$[\alpha]_D^{25} = +10.3°$ (c=0.5, methanol)

Example 41

Manufacture of preparation for injection:

(1S)-3-[2-(2-adamantyl)ethyl]-1,8,8-trimethyl-3-azabicyclo[3.2.1]octane hydrochloride I.Og was dissolved in distilled water for injection 1 liter, adjusted to PH 6–7 with 1N aqueous sodium hydroxide, sterilized, and filled each 5 ml in ampule to prepare a preparation for injection.

Example 42

| Manufacture of tablets: | |
|---|---|
| (1S)-3-[2-(2-adamantyl)ethyl]-1-,8,8-trimethyl-3-azabicyclo[3.2.1]octane hydrochloride | 50.0 mg |
| corn starch | 40.0 mg |
| crystalline cellulose | 80.0 mg |
| magnesium stearate | 0.5 mg |
| talc | 29.5 mg |

A tablet of 200 mg consisting of the above composition was prepared by means of dry tabletting.

Example 43

Production of (IR)-3-(1-naphthylacetyl)-1,8,8trimethyl-3-azabicyclo[3.2.1]octane:

Triethylamine 0.84 ml was added to a methylene chloride 20 ml solution of (lR)-1,8,8-trimethyl-3-azabicyclo[3.2.1] octane hydrochloride 0.95 g and stirred at O@C for 30 min. 1-naphthylacetic acid 0.93 g (5-0 mkf) and 1-ethyl-3-(3'-dimethylamino propyl) carbodiimide hydrochloride (WSC) 1.35 g (7.0 mill) were added thereto, then temperature of the reaction mixture was gradually changed to room temperature and stirred for 24 hours. The reaction mixture was washed with saturated aqueous sodium chloride solution and dried by anhydrous sodium sulfate. After removing the drying agent by filtration from organic solvent, the filtrate was concentrated in vacuo. The thus obtained residue was purified by means of silica gel (Wako gel C200, Wako Pure Chemical Co.) column chromatography, developer:chloroform) to obtain the product as white powder.

Yield: 1.09 g (Yield 67.7%)

Example 44

Production of (lR)-3-(2-naphthylacetyl)-1,8,8-trimethyl-3-azabicyclo[3.2.1]octane:

In Example 43, 2-naphthylacetic acid was used in place of 1-naphthylacetic acid to obtain the product as white powder.

Yield: 1.28 g (Yield 79.5%)

Example 45

Production of (lR)-3-[2-(1-naphthyl)ethyl]-1,8,8-trimethyl-3-azabicyclo[3.2.1]octane:

(1R)-3-(1-naphthylacetyl)-1,8,8-trimethyl-3-azabicyclo[3.2.1]octane 1.09 g (3.4 mill) was added to tetrahydrofuran (THF) 20 ml solution of lithium aluminum hydride 0.25 g (6.8 mill) and refluxed under heating for I hour. The reaction mixture was cooled and added 6N hydrochloric acid and 1N aqueous sodium hydroxide thereto. The precipitate was removed by filtration and the filtrate was concentrated in vacuo. The thus obtained residue was purified by means of silica gel (Wako gel C-200, Wako Pure Chemical Co.) chromatography (developer: chloroform:acetone=10:1) to obtain the product as colorless oily material.

Yield: 1.03 g (Yield 99.0%)

Two molar excess of hydrogen chloride methanol solution was added to the above compound and concentrated in vacuo. The residue was crystallized by diethyl ether to prepare hydrochloride.

$[\alpha]_D^{25}=+6.0°$ (c=0.5, methanol)

Example 46

Production of (lR)-3-[2-(1-naphthyl)ethyl]-1,8,8-trimethyl-3-azabicyclo[3.2.1]octane:

(1R)-3-(2-naphthylacetyl)-1,8,8-trimethyl-3-azabicyclo[3.2.1]octane 1.28 g (3.99 mill) was added to THF 25 ml solution of lithium aluminum hydride 0.30 g (7.89 mill) and refluxed under heating for I hour. The reaction mixture was cooled and added 6N hydrochloric acid and 1N aqueous sodium hydroxide thereto. The precipitate was removed by filtration and the filtrate was concentrated in vacuo. The thus obtained residue was purified by means of silica gel (Wako gel C200, Wako Pure Chemical Co.) chromatography (developer chloroform: acetone=10:1) to obtain the product as colorless oily material.

Yield: 1.22 g (Yield 100%)

The compound was treated by the same method as of in Example 45 to obtain hydrochloride.

$[\alpha]_D^{25}=+3.2°$ (c=0.5, methanol)

Example 47

Production of (1R)-3-[2-(2-pyridyl)ethyl]-1,8,8-trimethyl-3-azabicyclo[3.2.1]octane:

Triethylamine 1.75 ml (12.6 mill) was added to a methylene chloride 20 ml solution of (1R)-1,8,8-trimethyl-3-azabicyclo[3-2-1]octane hydrochloride 0.95 g (5.0 mill) and 2-pyridylacetic acid hydrochloride 0.96 g (5.5 mill) and stirred at 0@C for 30 min. WSC 1.35 g (7.0 mill) was added therein, then temperature of the reaction mixture was gradually changed to room temperature and stirred for 24 hours. The reaction mixture was washed with saturated aqueous sodium chloride solution and dried by anhydrous sodium sulfate. After filtering the drying agent, the filtrate was concentrated in vacuo to obtain crude (lR)-3-(2-pyridylacetyl)-1,8,8-trimethyl-3-azabicyclo[3.2.1]octane. The concentrate was added to THF 20 ml solution of lithium aluminum hydride 0.29 g (7.6 mill) and refluxed under heating for 1 hour. The reaction mixture was cooled, then water was added thereto and the insoluble material was removed by filtration. The filtrate was concentrated in vacuo. The thus obtained residue was purified by means of silica gel column chromatography (Wako gel, C200, chloroform:methanol 10:1–5:1) to obtain the product as yellowish oily material.

Yield: 0.20 g (Yield 15.5% by 2 steps)

The product was treated by the same way as of in Example 45 to obtain the hydrochloride.

$[\alpha]_D^{25}=+5.9°$ (c=0.5, methanol)

Example 48

Production of (lR)-3-[2-(4-pyridyl) ethyl]-1,8,8-trimethyl-3-azabicyclo[3.2.1]octane:

Example 47 was repeated except that (lR)-1,8,8-trimethyl-3-azabicyclo[3.2.1]octane hydrochloride 0.95 g (5.0 mill) and 4-pyridyl acetic acid hydrochloride 0.96 g (5.5 mill) were used and a crude substance obtained from the reaction mixture was purified by silica gel column chromatography (Wako gel, C200, chloroform:methanol=50:1), and the other processes were taken almost same way as of in Example 47 to obtain the product as yellowish oily material.

Yield: 0.37 g (Yield 28.7% by 2 steps)

The product was treated by the same method as of in Example 45 to obtain the hydrochloride.

$[\alpha]_D^{25}=+7.9°$ (c=0.5, methanol)

Referential Example 31

Production of (1S)-1,8,8-trimethyl-3-azabicyclo[3.2.1] octan-2-one:

(1S)-camphor 8.31 g (54.6 mill) and hydroxylamine-0-sulfonic acid 9.25 g (81.9 mill) in acetic acid 200 ml were refluxed under heating for 7 hours. The reaction mixture was concentrated in vacuo and the residue dissolved in chloroform was washed with saturated aqueous sodium bicarbonate solution. Organic layer was dried by anhydrous sodium sulfate, which was thereafter removed by filtration, then the filtrate was concentrated in vacuo. The thus obtained residue was purified by means of silica gel column chromatography (Wako gel, C200, chloroform) to obtain the product as white needle crystal. Yield: 5.57 g (Yield 55.6%)

$[\alpha]_D^{25}=+25.0°$ (c=0.5, methanol)

Referential Example 32

Production of (1S)-1,8,8-trimethyl-3-azabicyclo[3.2.1] octane:

37

(IS)-1,8,8-trimethyl-3-azabicyclo[3.2.1]octan-2-one 1.93 g (11.6 mM) was added in THF 20 ml solution of lithium aluminum hydride 0.88 g (23 m,@, and the reaction mixture was refluxed under heating for 22 hours. The reaction mixture was cooled and added 6N HCL and 5N NAOH therein to alkalize the mixture. Insoluble material was removed by filtration and the filtrate was extracted with ether, dried by anhydrous sodium sulfate. The drying agent was removed by filtration and the filtrate was concentrated in vacuo to obtain the product. Yield: 1.70 g (Yield 96.6%)

$[\alpha]_D^{25} = -17.2°$ (c=0.5, methanol)

Example 49

Production of (IS)-3-[2-(1-naphthyl)ethyl]-1,8,8-trimethyl-3-azabicyclo-[3.2.1]octane:

Methylene chloride 20 ml solution of 2-(1-naphthyl)ethyl alcohol 0.87 g (5.0 mill) was cooled to 0° C., then methanesulfonyl chloride 0.47 ml (6.1 mill) and triethylamine 0.84 ml (6.0 mill) were added thereto. Temperature of the reaction mixture was gradually changed to room temperature and stirred for 21 hours. The reaction mixture was concentrated in vacuo to obtain the crude mesylate. (IS)-1, 8,8-trimethyl-3-azabicyclo[3.2.1]octane hydrochloride 0.95 g (5.0 mill) and potassium carbonate 2.08 g (15.0 mill) were added thereto, then prepared acetonitrile 20 ml solution. The solution was refluxed under heating for 18 hours. Insoluble material was removed by filtration and the filtrate was concentrated in vacuo. The thus obtained residue was purified by means of silica gel column chromatography (Wako gel, C200, chloroform) to obtain the product.

Yield: 0.92 g (Yield 59.4%)

The product was treated by the same way as of in Example 45 to obtain the hydrochloride.

$[\alpha]_D^{25} = -5.5°$ (c=0.5, methanol)

Example 50

Production of (IS)-3-[2-(2-naphthyl)ethyl]-1,8,8-trimethyl-3-azabicyclo[3.2.1]octane:

Triethylamine 0.84 ml (6.0 mill) was added to a methylene chloride 20 ml solution of (IS)-1,8,8-trimethyl-3-azabicyclo[3.2.1]octane hydrochloride 0.95 g (5.0 mill) and stirred at 0° C. for 30 min. β-naphthylacetic acid 0.93 g (5.0 mill) and WSC 1.35 g (7.04 mill) were added therein, then temperature of the reaction mixture was gradually changed to room temperature and stirred for 23 hours. The reaction mixture was washed with saturated aqueous sodium chloride solution and dried by anhydrous sodium sulfate. After the drying agent was removed by filtration, the filtrate was concentrated in vacuo to obtain crude (1S)-3-(2-naphthylacetyl)-1,8,8-trimethyl-3-azabicyclo[3.2.]octane. The concentrate was added to THF 30 ml solution of lithium aluminum hydride 0.39 g (10.3 mill) and refluxed under heating for I hour. The reaction mixture was cooled, then water was added thereto and the insoluble material was removed by filtration. The filtrate was concentrated in vacuo. The thus obtained residue was purified by means of silica gel column chromatography (Wako gel, C200, chloroform) to obtain the product.

Yield: 1.11 g (Yield 72.1%)

The product was treated by the same way as of in Example 45 to obtain the hydrochloride.

$[\alpha]_D^{25} = -6.2°$ (c=0.5, methanol)

Example 51

Production of (1S)-3-[2-(2-pyridyl)ethyl]-1,8,8-trimethyl-3-azabicyclo[3.2.1]octane:

38

Triethylamine 3.50 ml (25.1 mill) was added to a methylene chloride 40 ml solution of (1S)-1,8,8-trimethyl-3-azabicyclo[3.2.]octane hydrochloride 1.9 og (10.0 mill) and 2-pyridylacetic acid hydrochloride 1.92 g (11.6 mill) and stirred at 0° C. for 30 min. WSC 2.70 g (14.1 mm) was added therein, then temperature of the reaction mixture was gradually changed to room temperature and stirred for 48 hours. The reaction mixture was washed with saturated aqueous sodium chloride solution and dried by anhydrous sodium sulfate. After the drying agent was removed by filtration, the filtrate was concentrated in vacuo to obtain crude (1S)-3-(2-pyridylacetyl)1,8,8-trimethyl-3-azabicyclo[3.2.1]octane. The concentrate was added to THF 60 ml solution of lithium aluminum hydride 0.77 g (20.3 mill) and refluxed under heating for 1 hour. The reaction mixture was cooled, then water was added thereto and the insoluble material was removed by filtration. The filtrate was concentrated in vacuo. The thus obtained residue was purified by means of silica gel column chromatography (Wako gel, C200, chloroform: acetone =10:1) to obtain the product as orange colored oily material.

Yield: 0.99 g (Yield 38.2%)

The product was treated by the same way as of in Example 45 to obtain the hydrochloride.

$[\alpha]_D^{25} = -18.2°$ (c=0.5, methanol)

Example 52

Production of (1S)-3-[2-(3-pyridyl)ethyl]-1,8,8-trimethyl-3-azabicyclo[3.2.1]octane:

Triethylamine 3.20 ml (23.0 mill) was added to a methylene chloride 40 ml solution of (IS)-1,8,8-trimethyl-3-azabicyclo[3.2.1]octane hydrochloride 1.74 g (9.18 mill) and 3-pyridylacetic acid hydrochloride 1.76 g (10.1 mill) and stirred at 0° C. for 30 min. WSC 2.47 g (12.9 mill) was added therein, then temperature of the reaction mixture was gradually changed to room temperature and stirred for 46 hours. The reaction mixture was washed with saturated aqueous sodium chloride solution and dried by anhydrous sodium sulfate. After the drying agent was removed by filtration, the filtrate was concentrated in vacuo to obtain crude (IS)-3-(3-pyridylacetyl)-1,8,8-trimethyl-3-azabicyclo[3.2.1]octane. The concentrate was added to THF 60 ml solution of lithium aluminum hydride 0.77 g (20.3 mill) and refluxed under heating for 3 hours. The reaction mixture was cooled, then water was added thereto and the insoluble material was removed by filtration. The filtrate was concentrate in vacuo. The thus obtained residue was purified by means of silica gel column chromatography (Wako gel, C200, chloroform:acetone=10:1–5:1) to obtain the product as yellowish oily material.

Yield: 0.46 g (Yield 19.4%)

The product was treated by the same way as of in Example 45 to obtain the hydrochloride.

$[\alpha]_D^{25} = -3.7°$ (c=0.5, methanol)

Example 53

Production of (1S)-3-[2-(4-pyridyl)ethyl]-1,8,8-trimethyl-3-azabicyclo[3.2.1]octane:

Triethylamine 1.75 ml (12.6 mill) was added to a methylene chloride 20 ml solution of (1S)-1,8,8-trimethyl-3-azabicyclo[3.2.1]octane hydrochloride 0.95 g (5.0 mill) and 4-pyridylacetic acid hydrochloride 0.96 g (5.5 mill) and stirred at 0° C. for 30 min. WSC 1.35 g (7.04 mill) was added thereto, then temperature of the reaction mixture was gradually changed to room temperature and stirred for 24 hours. The reaction mixture was washed with saturated aqueous sodium chloride solution and dried by anhydrous sodium sulfate. After the drying agent was removed by filtration, the filtrate was concentrated in vacuo to obtain crude (1S)-3-(4-pyridylacetyl)-1,8,8trimethyl-3-azabicyclo [3.2.1]octane. The concentrate was added to THF 30 ml solution of lithium aluminum hydride 0.39 g (10.3 mill) and refluxed under heating for 3 hours. The reaction mixture was cooled, then water was added thereto and the insoluble material was removed by filtration. The filtrate was concentrated in vacuo. The thus obtained residue was purified by means of silica gel column chromatography (Wako gel, C200, chloroform acetone=10:1) to obtain the product as orange colored oily material. Yield: 0.35 g (Yield 27.1%)

The product was treated by the same way as of in Example 45 to obtain the hydrochloride.

$[\alpha]_D^{25}=-11.0°$ (c=0.5, methanol)

Example 54

Production of (1S)-3-[2-(1,3-benzodioxol-5-yl)ethyl]-1,8,8-trimethyl-3-azabicyclo[3.2.1]octane:

Triethylamine 0.54 ml (3.9 mill) was added to a methylene chloride 15 ml solution of (IS)-1,8,8-trimethyl-3-azabicyclo[3-2-1]octane hydrochloride 0.52 g (2–8 mill) and stirred at 0° C. for 30 min. 1,3-benzodioxole-5-acetic acid 0.60 g (3.3 mill) and WSC 0.74 g (3.9 mill) were added therein, then temperature of the reaction mixture was gradually changed to room temperature and stirred for 21 hours. The reaction mixture was washed with saturated aqueous sodium chloride solution and dried by anhydrous sodium sulfate. After the drying agent was removed by filtration, the filtrate was concentrated in vacuo to obtain crude (IS)-3-(1,3-benzodioxole-5-ylacetyl)-1,8,8-trimethyl-3-azabicyclo [3.2.1]octane. The concentrate was added to THF 10 ml solution of lithium aluminum hydride 0.21 g (5.5. mM) and refluxed under heating for 2.5 hours. The reaction mixture was cooled, then water was added thereto and the insoluble material was removed by filtration. The filtrate was concentrated in vacuo. The thus obtained residue was purified by means of flash silica gel column chromatography (Merck, silica gel 60:230–600 mesh, chloroform) to obtain the product as colorless oily material. Yield: 0.66 g (Yield 78.2%)

The product was treated by the same way as of in Example 45 to obtain the hydrochloride.

$[\alpha]_D^{25}=-6.5°$ (c=0.5, methanol)

Example 55

Production of (1S)-3-[2-(2-thienyl)ethyl]-1,8,8-trimethyl-3-azabicyclo[3.2.1]octane:

Triethylamine 0.34 ml (2.4 mill) was added to a methylene chloride 10 ml solution of (IS)-1,8,8-trimethyl-3-azabicyclo[3.2.1]octane hydrochloride 0.38 g (2.0 mill) and stirred at 0° C. for 30 min. 2-thienyl acetic acid 0.35 g (2.5 mill) and WSC 0.54 g (2.8 mill) were added therein, then temperature of the reaction mixture was gradually changed to room temperature and stirred for 21 hours. The reaction mixture was washed with saturated aqueous sodium chloride solution and dried by anhydrous sodium sulfate. After the drying agent was removed by filtration, the filtrate was concentrated in vacuo to obtain crude (1S)-3-(2-thienylacetyl)-1,8,8-trimethyl-3-azabicyclo[3-2-1]octane. The concentrate was added to THF 15 ml solution of lithium aluminum hydride 0.16 g (4.2 mill) and refluxed under heating for I hour. The reaction mixture was cooled, then water was added thereto and the insoluble material was removed by filtration. The filtrate was concentrated in vacuo. The thus obtained residue was purified by means of silica gel column chromatography (Wako gel, C200, chloroform) to obtain the product as pale yellowish oily material. Yield: 0.37 g (Yield 65.8 %)

The product was treated by the same way as of in Example 45 to obtain the hydrochloride.

$[\alpha]_D^{25}=-12.8°$ (c=0.5, methanol)

Example 56

Manufacture of preparation for injection:

(1S)-3-[2-(2-naphthyl)ethyl]-1,8,8-trimethyl-3-azabicyclo[3.2.1]octane hydrochloride 1.0 g was dissolved in distilled water for injection 1 liter, adjusted to PH 6–7 with 1N aqueous sodium hydroxide, sterilized, and filled each 5 ml in ampule to prepare a preparation for injection.

Example 57

| Manufacture of tablets: | |
|---|---|
| (1S)-3-[2-(2-naphthyl)ethyl]-1,8,8-trimethyl-3-azabicyclo[3.2.1]octane hydrochloride | 50.0 mg |
| corn starch | 40.0 mg |
| crystalline cellulose | 80.0 mg |
| magnesium stearate | 0.5 mg |
| talc | 29.5 mg |

A tablet of 200 mg consisting of the above composition was prepared by means of dry tabletting.

Example 58

Production of cis-(1S)-3-[2-(5-hydroxy-2-adamantyl) ethyl]-1,8,8trimethyl-3-azabicyclo[3.2.1]octane and trans-(1S)-3-[2-(5-hydroxy-2-adamantyl)ethyl]-1,8,8-trimethyl-3-azabicyclo[3.2.1]octane:

A mixture of stereoisomer (a mixture consisting of I:1, measured by gas chromatography) of (1S)-3-[2-(5-hydroxy-2-adamantyl)ethyl]-1,8,8trimethyl-3-azabicyclo[3.2.1] octane obtained in Example 23, 1.00 g was isolated and purified by silica gel column chromatography (Merck, silica gel 60, Art 9385, 150 g, chloroform:ethanol=20:1–5:1) to obtain the first eluted stereoisomer (compound No. 58a and the later eluted stereoisomer (compound No. 58,8), each 50 mg, respectively.

Rf values of the compound No. 58α and the compound No. 58β were 0.40 and 0.29, respectively.

Each of the stereoisomer was dissolved in methanol solution of hydrogen chloride, concentrated and crystallized by adding ether to obtain each of hydrochloride.

The thus obtained hydrochloride of the compound No. 58,8 was recrystallized from methanol-di-ethyl ether, and the obtained colorless cylindrical crystal was subjected to X-ray analysis by the following method.

X-ray analyzer: Mac Science Inc., MXCI8.

Structural analysis: Crystal-GM (Version 6.1).

The thus obtained Ortep figure is shown in FIG. 1, in which the compound No. 58β is trans-configuration. Accordingly the compound No. 58α is cis-configuration.

Example 59

Production of cis-(1R)-3-[2-(5-hydroxy-2-adamantyl) ethyl]-1,8,8trimethyl-3-azabicyclo[3.2.1]octane and trans-(IR)-3-[2-(5-hydroxy-2-adamantyl)ethyl]-1,8,8-trimethyl-3-azabicyclo[3.2.1]octane:

A mixture of stereoisomer (a mixture consisting of 1:1, measured by gas chromatography) of (1R)-3-[2-(5-hydroxy-2-adamantyl)ethyl]-1,8,8trimethyl-3-azabicyclo[3.2.1] octane obtained in Example 31, 1.00 g was isolated and purified by silica gel column chromatography (Merck, silica gel 60, Art 9385, 150 g, chloroform:ethanol=20:1–5:1) to obtain the first eluted stereoisomer (compound No. 59a ) and the later eluted stereoisomer (compound No. 59,8), each 50 mg, respectively.

Rf values of the compound No. 59α and the compound No. 59β were 0.40 and 0.29, respectively.

The thus obtained each stereoisomer was treated by the same way as of in Example 58 to obtain each compound in the form of hydrochloride.

Example 60

Production of cis-(1S)-3-[2-(5-methoxy-2-adamantyl)ethyl]-1,8,8trimethyl-3-azabicyclo[3.2.1]octane and trans-(1S)-3-[2-(5-methoxy-2-adamantyl)ethyl]-1,8,8-trimethyl-3-azabicyclo[3.2.1]octane:

A mixture of stereoisomer (a mixture consisting of 1:1, measured by gas chromatography) of (IS)-3-[2-(5-methoxy-2-adamantyl)ethyl]-1,8,8trimethyl-3-azabicyclo[3.2.1] octane obtained in Example 24, was isolated and purified by the same way as of in Example 58 to obtain the first eluted stereoisomer (compound No. 60α) and the later eluted stereoisomer (compound No. 60β), respectively.

The thus obtained each stereoisomer was treated by the same way as of in Example 1 to obtain each compound in the form of hydrochloride.

Configuration of transform or cis-form of the compounds No. 60α and 60β was determined by the following experiment.

DMF 3 ml solution of trans-(1S)-3-[2-(5-hydroxy-2-adamantyl)ethyl]-1,8,8-trimethyl-3-azabicyclo[3.2.1]octane (compound No. 58,8) 113 mg was added in a DMF suspension 2.5 ml of sodium hydride (60%, oil dispersion) 41.0 mg at 0° C., and after changing the temperature to room temperature, the reaction mixture was stirred for 1.1 hour. Methyl iodide 70 gI was added to the reaction mixture and stirred at the same temperature for 20 hours. The reaction mixture was cooled to O@C, aqueous saturated ammonium chloride and water were added in this order, then extracted with chloroform. Organic layer was separated and solvent was distilled off in vacuo. Residue was purified by means of silica gel column chromatography to obtain trans (IS)-3-[2-(5-methoxy-2-adamantyl)ethyl]-1,8,8-trimethyl-3-azabicyclo[3.2.1]octane. Yield: 33. gmg (Yield 29%).

The compound was treated by the same way as of the method hereinbefore to obtain the hydrochloride. $^1$H-NMR data of the product and those of the compounds No. 60α and 60β were compared with each other, and the compound No. 60β was defined as the trans configuration.

Example 61

Production of cis-(1R)-3-[2-(5-methoxy-2-adamantyl)ethyl]-1,8,8trimethyl-3-azabicyclo[3.2.1]octane and trans-(1R)-3-[2-(5-methoxy-2-adamantyl)ethyl]-1,8,8-trimethyl-3-azabicyclo[3.2.1]octane:

A mixture of stereoisomer (a mixture consisting of 1:1, measured by gas chromatography) of (1R)-3-[2-(5-methoxy-2-adamantyl)ethyl-1,8,8trimethyl-3-azabicyclo[3.2.1]octane obtained in Example 30, was isolated and purified by the same way as of in Example 58 to obtain the first eluted stereoisomer (compound No. 61α) and the later eluted stereo-isomer (compound No. 61β), respectively.

The thus obtained each stereoisomer was treated by the same way as of in Example I to obtain each compound in the form of hydrochloride.

Example 62

Production of cis-(1S)-3-[2-(5-chloro-2-adamantyl)ethyl]-1,8,8-trimethyl-3-azabicyclo[3.2.1]octane (compound No. 62):

Thionyl chloride 5 ml was added to cis-(1S)-3-[2-(5-hydroxy-2-adamantyl)ethyl]-1,8,8-trimethyl-3-azabicyclo[3.2.1]octane (compound No. 58a) which is the first eluted compound obtained in Example 58, 85.0 mg and refluxed under heating for 4.5 hours. Reaction mixture was concentrated in vacuo, and after converting to alkaline PH by adding IN sodium hydroxide to the residue, the mixture was extracted with chloroform. The extract was dried by adding anhydrous sodium sulfate, and the drying agent was removed off by filtration. The residue obtained by concentrating the filtrate in vacuo was purified by silica gel column chromatography (Wako gel, C200, chloroform:acetone 20:1) to obtain the product. Yield: 49.4 mg (yield 55%).

The compound was treated by the same way as of in Example 58 to obtain the hydrochloride.

Example 63

Production of trans-(IS)-3-[2-(5-chloro-2-adamantyl)ethyl]-1,8,8-trimethyl-3-azabicyclo[3.2.1]octane (compound No. 63):

Thionyl chloride 5 ml was added to trans-(IS)-3-[2-(5-hydroxy-2-adamantyl)ethyl]-1,8,8-trimethyl-3-azabicyclo[3.2.1]octane (compound No. 58β) which is the later eluted compound obtained in Example 58, 90.0 mg and refluxed under heating for 4.5 hours. Reaction mixture was concentrated in vacuo, and after converting to alkaline PH by adding 1N sodium hydroxide to the residue, the mixture was extracted with chloroform. The extract was dried by adding anhydrous sodium sulfate, and the drying agent was removed off by filtration. The residue obtained by concentrating the filtrate in vacuo was purified by silica gel column chromatography (Wako gel, C200, chloroform: acetone 20:1) to obtain the product.

Yield: 43.7 mg (Yield 46)

The compound was treated by the same way as of in Example 58 to obtain the hydrochloride.

Example 64

Production of stereoisomer of (1R)-3-[2-(5-chloro-2-adamantyl)ethyl]-1,8,8-trimethyl-3-azabicyclo[3.2.1]octane (compound No. 64):

Thionyl chloride 5 ml was added to stereoisomer of (IR)-3-[2-(5-hydroxy-2-adamantyl)ethyl]-1,8,8-trimethyl-3-azabicyclo[3.2.1]octane (compound No. 59a) which is the first eluted compound obtained in Example 59, 86.0 mg and refluxed under heating for 4.5 hours. Reaction mixture was concentrated in vacuo, and after converting to alkaline PH by adding 1N sodium hydroxide to the residue, the mixture was extracted with chloroform. The extract was dried by adding anhydrous sodium sulfate, and the drying agent was removed off by filtration. The residue obtained by concentrating the filtrate in vacuo was purified by silica gel column chromatography (Wako gel, C200, chloroform acetone= 20:1) to obtain the product. Yield: 51.8 mg (Yield 57%).

The compound was treated by the same way as of in Example 58 to obtain the hydrochloride.

Example 65

Production of stereoisomer of (IR)-3-[2-(5-chloro-2-adamantyl) ethyl]-1,8,8-trimethyl-3-azabicyclo[3.2.1] octane (compound No. 65):

Thionyl chloride 5 ml was added to (1R)-3-[2-(5-hydroxy-2-adamantyl) ethyl]-1,8,8-trimethyl-3-azabicyclo[3.2.1]octane (compound No. 59,8) which is the later eluted compound obtained in Example 59, 92.0 mg and refluxed under heating for 4.5 hours. Reaction mixture was concentrated in vacuo, and after converting to alkaline pH by adding 1N sodium hydroxide to the residue, the mixture was extracted with chloroform. The extract was dried by adding anhydrous sodium sulfate, and the drying agent was removed off by filtration. The residue obtained by concentrating the filtrate in vacuo was purified by silica gel column chromatography (Wako gel, C200, chloroform:acetone 20:1) to obtain the product.

Yield: 55.1 mg (Yield 57%).

The compound was treated by the same way as of in Example 58 to obtain the hydrochloride.

Example 66

Production of cis-(1S)-3-[2-(5-phenyl-2-adamantyl)ethyl]-1,8,8trimethyl-3-azabicyclo[3.2.1]octane and trans-(1S)-3-[2-(5-phenyl-2-adamantyl)ethyl]-1,8,8-trimethyl-3-azabicyclo[3.2.1]octane:

A mixture of stereoisomer (a mixture consisting of 1:1, measured by gas chromatography) of (1S)-3-[2-(5-phenyl-2-adamantyl)ethyl]-1,8,8trimethyl-3-azabicyclo[3.2.1]octane obtained in Example 26, was isolated and purified by the same way as of in Example 58 to obtain the first eluted stereoisomer (compound No. 66a) and the later eluted stereoisomer (compound No. 66,8), respectively.

The thus obtained each stereoisomer was treated by the same way as of in Example 1 to obtain each compound in the form of hydrochloride.

Configuration of trans-form or cis-form of the compounds No. 66α and 66β was determined by the following experiment.

A mixed solution of trans-(1S)-3-[2-(5-hydroxy-2-adamantyl)ethyl]-1,8,8-trimethyl-3-azabicyclo[3.2.1]octane (compound No. 58 6) 890 mg, sulfuric acid 0.14 ml, acetic acid gml and benzene 45 ml were stirred at room temperature for 4.3 hours. Further adding acetic acid 10 ml, the reaction mixture was stirred at the same temperature for 3 hours and refluxed under heating for 16 hours. After removing off the benzene in vacuo, water and 10% aqueous sodium hydroxide and extract with chloroform. Organic layer was washed with water and distilled off in vacuo. The thus obtained residue was treated by means of silica gel column chromatography to obtain crude substance containing trans (1S)3-[2-(5-phenyl-2-adamantyl)ethyl]-1,8,8-trimethyl-3-azabicyclo[3.2.1]octane.

The crude substance was decomposed by adding 10% aqueous sodium hydroxide and purified by means of silica gel column chromatography (Merck, silica gel 60, Art. 9385, chloroform) to obtain trans (1S)-3[2-(5-phenyl-2-adamantyl)ethyl]-1,8,8-trimethyl-3-azabicyclo[3-2-1]octane.

Yield: 13.4 mg (Yield 1%).

The compound was treated by the same way as of the method hereinbefore to obtain the hydrochloride.

1H-NMR data of the product and those of the compounds No. 66α and 66β were compared with each other, and the compound No..66,8 was defined as the trans configuration.

Example 67

Production of cis-(1R)-3-[2-(5-phenyl-2-adamantyl)ethyl]-1,8,8trimethyl-3-azabicyclo[3.2.1]octane and trans-(1R)-3-[2-(5-phenyl-2-adamantyl)ethyl]-1,8,8-trimethyl-3-azabicyclo[3.2.1]octane: A mixture of stereoisomer (a mixture consisting of 1:1, measured by gas chromatography) of (1R)-3-[2-(5-phenyl-2-adamantyl)ethyl]-1,8,8-trimethyl-3-azabicyclo[3.2.1]octane obtained in Example 33. Was isolated and purified by the same way as of in Example 58 to obtain the first eluted streoisomer (compound No. 67α) and the later eluted stereoisomer (compound No. 67β), respectively.

The thus obtained each stereoisomer was treated by the same way as of in Example 58 to obtain each compound in the form of hydrochloride.

TABLE 5

| Ref. No. | $^1$H-NMR (CDCl$_3$) δ (ppm) | MS |
| --- | --- | --- |
| 1 | 0.95(3H. s), 1.04(3H. s), 1.10(3H, s), 1.5~1.7(1H, m) 1.7~1.8(1H, m), 1.8~1.9 (1H, m), 2.0~2.2(2H, m), 3.00(1H, d, J=10.9Ha), 3.48(1H, dd, J=3.0, 10.9Hz), 5.50(1H, bs) | (FAB) 168 (MH$^+$) |
| 2 | 0.75(3H, s), 0.86(3H, s), 1.03(3H, s), 1.4~1.7(4H, m), 1.8~2.0(1H, m), 2.13 (1H, d, J=12.9Hz), 2.42(1H, dd, J=3.0, 12.9Hz) 2.86(1H, d, J=13.2Hz), 3.16 (1H, d, J=12.9Hz) | (EI) 153 (M$^+$) |
| 3 | 1.5~1.8(8H, m), 2.38(2H, dd, J=5.6, 6.3Hz), 2.88(2H, dd, J=5.9, 6.3Hz), 3.68 (3H, s), 5.67(1H, s) | |
| 4 | 1.1~1.9(16H, m), 3.67(2H, t, J=6.6Hz) | |
| 5 | 1.4~1.6(10H, m), 2.32(2H, dd, J=5.9, 6.3Hz), 2.76(2H, t, J=6.3Hz), 3.68(3H, s), 5.72(1H, s) | |
| 6 | 1.2~1.8(14H, m), 1.9~2.1(1H, m), 2.22(2H, d. J=7.6Hz), 3.66(3H, s) | |
| 7 | 1.2~1.8(14H, m), 2.0~2.2(1H, m), 2.26(2H, d, J=7.3Hz) | |
| 8 | 1.8~2.0(12H, m), 2.44(1H, bs), 3.68 (3H, s), 4.06(1H, bs), 5.59(1H, x) | |
| 9 | 1.5~1.9(13H, m), 2.23(1H, dd, J=7.3, 7.9Hz), 2.46(2H, d, J=7.6Hz), 3.66(3H, s) | |
| 10 | 1.56(2H, d, J=11.9Hz), 1.6~1.9(12H, m), 2.24(1H, t, J=7.3Hz), 2.50(2H, d, J=7.3Hz) | (FAB) 193 (M-H)$^-$ |
| 11 | 1.1~1.2(1H, m), 1.5~2.0(16H, m), 3.67(2H, dd, J=6.1, 12.0 Hz) | |
| 12 | 1.4~2.1(12H, m), 2.36(1H, bs), 3.68 (3H, s), 3.99(1H, bs), 5.64(1H, bs) | |
| 13 | 1.4~1.8(14H, m), 2.02(1H, dd, J=7.3, 7.9Hz), 2.46(2H, d, J=7.9 Hz), 3.66(3H, s) | |
| 14 | 1.4~1.9(14H, m), 2.03(1H, t, J=7.6 Hz), 2.50(2H, d, J=7.6Hz) | |
| 15 | 1.54(1H, s), 1.7~1.9(10H, m), 2.25 (1H, bs), 2.61(1H, bs), 3.69(3H, s), 4.33(1H, bs), 5.61(1H, s) | (FAB) 223 (MH$^+$) |
| 16 | 1.4~2.2(15H, m), 2.41(1H, d, J=7.6 Hz), 2.45(1H, d, J=7.6Hz), 3.67(1.5H, s), 3.67(1.5H, s) | (FAB) 223 (M-H)$^-$ |
| 17 | 1.4~2.2(15H, m), 2.45(1H, d, J=7.6 Hz), 2.49(1H, d, J=7.6Hz) | (FAB) 209 (M-H)$^-$ |
| 18 | 1.9~2.1(10H, m), 2.35(1H, bs), 2.64 (2H bs), 3.26(3H, s) | |
| 19 | 1.7~1.9(10H, m), 2.26(1H, bs), 2.63 (1H, bs), 3.23(3H, s), 3.69(3H, s), 4.24 (1H, bs), 5.61(1H, s) | (FAB) 237 (MH$^+$) |
| 20 | 1.3~2.2(14H, m), 2.41(1H, d, J=7.3 Hz), 2.45(1H, d, J=7.6Hz), 3.23(1 5H, s), 3.23(1.5H, s), 3.67(1.5H, s), 3.67 (1.5H, s) | (FAB) 237 (M-H)$^-$ |
| 21 | 1.3~2.2(14H, m), 2.38(1H, d, J=7.9 Hz), 2.41(1H, d, J=7.6 Hz), 3.17(3H, s) | |
| 22 | 1.8~2.1(10H, m), 2.20(1H, bs), 2.61 (1H, bs), 3.70(3H, s), 4.23(1H, bs), 5.66(1H, s), 7.1~7.4(5H, m) | (FAB) 283 (MH$^+$) |

TABLE 5-continued

| Ref. No. | $^1$H-NMR (CDCl$_3$) δ (ppm) | MS |
|---|---|---|
| 23 | 1.7~2.3(14H, m), 2.48(1H, d, J=7.6 Hz), 2.53(1H, d, J=7.6 Hz), 3.67(1.5H, s), 3.75(1.5H, s), 7.1~7.4(5H, m) | (FAB) 285 (MH$^+$) |
| 24 | 1.5~2.1(14H, m), 2.41(1H, d, J=7.6 Hz), 2.45(1H, d, J=7.6 Hz), 7.1~7.4 (5H, m) | |
| 25 | 1.6~2.2(11H, m), 2.41(0.5H, bs), 2.46 (0.5H, bs), 3.69(3H, s), 3.70(3H, s), 4.01(1H, bs), 4.08(1H, bs), 5.67(0.5H, s), 5.79(0.5h, s) | (FAB) 223 (MH$^+$) |
| 26 | 1.4~2.2(16H, m), 3.66(1.5H, s), 3.68 (1.5H, s), 3.93(1H, bs) | |
| 28 | 1.6~2.2(9H, m), 2.44(1H, bs), 2.56 (1H, bs), 2.98(0.5H, bs), 2.08(0.5H, bs), 3.68(1H, s), 3.71(1H, s), 3.72(1H, s), 4.06(0.5H, bs), 4.74(0.5H, bs), 5.59 (0.5H, s), 5.70(0.25H, s), 5.76(0.25H, s), 7.1~7.5(5H, m) | (FAB) 283 (MH$^+$) |
| 29 | 1.5~2.6(15H, m), 3.0~3.1(1H, m), 3.66(1H, s), 3.70(1H, s), 3.71(1H, s), 7.1~7.4(5H, m) | |
| 30 | 1.5~2.6(15H, m), 3.0~3.1(1H, m), 7.1 ~7.5(5H, m) | (FAB) 269 (M-H)$^-$ |
| 31 | 0.95(3H, s, CH$_3$), 1.04(3H, s, CH$_3$), 1.10 (3H, s, CH$_3$), 1.5~1.7(1H, m. CH$_2$), 1.7 1.8 1H, m, CH$_2$), 1.8~1.9(1H, m. CH) , 2.0~2.2(2H, m, CH$_2$), 3.00(1H, d, CH$_2$, J=10.9Hz), 3.48(1H, dd, CH$_2$, J=3.0, 10.9 Hz), 5.50(1H, bs, NH) | (FAB) 168 (MH$^+$) |
| 32 | 0.75(3H, s, CH$_3$), 0.86(3H, s, CH$^3$), 1.03 (3H, s, CH$_3$), 1.4~1.7(4H, m, CH$_2$x2), 1.8 ~2.0(1H, m, CH), 2.13(1H, d, CH$_2$, J=12.9Hz), 2.42(1H, dd, CH$_2$), J=3.0, 12.9Hz), 2.86(1H, d, CH$_2$, J=13.2Hz), 13.16(1H, d, CH$_2$, J=12.9Hz) | (FI) 153 (M$^+$ |

Data of the compounds in the referential examples 16, 17, 20, 21, 23 and 24 is shown in a stereoisomer (mixture of 1:1 measured by gas chromatography) and data of the compound in the referential examples 25–30 is a mixture of stereoisomer.

TABLE 6

| Exam. No. | $^1$H-NMR (CDCl$_3$) δ (ppm) | MS |
|---|---|---|
| 1 | 0.77(3H, s), 0.84(3H, s), 0.89(3H, s), 1.2~2.1(22H, m), 2.2~2.8(6H, m) | (FAB) 316 (MH$^+$) |
| 2 | 0.77(3H, s), 0.84(3H, s), 0.89(3H, s) 0.9~1.9(14H, m), 2.1~2.4(4H, m), 2.49, (1H, s), 2.50(1H, s) | (FAB) 276 (M$^+$) |
| 3 | 0.77(3H, s), 0.84(3H, s), 0.89(3H, s), 0.9~1.2(2H, m), 1.4~1.8(14H, m), 2.19(1H, d, J=10.6 Hz), 2.25(1H, d, J=10.6Hz), 2.35(2H, t, J=7.8Hz), 2.48 (1H, s), 2.49(1H, s) | (FAB) 250 (MH$^+$) |
| 4 | 0.77(3H, s), 0.85(3H, s), 0.89(3H, s) 1.1~1.4(6H, m), 1.5~1.8(12H, m), 2.18(1H, d, J=10.2Hz), 2.25(1H, d, J=10.6Hz), 2.36(2H, dd, J=6.9, 7.3Hz), 2.48(2H, s) | (FAB) 264 (MH$^+$) |
| 5 | 0.86(1.5H, s), 0.87(1.5H, s), 0.89(3H, s), 0.99(3H, s), 1.1~2.0(12H, m), 2.1 ~2.3(4H, m), 2.80(1H, d, J=12.9 Hz), 3.07(1H, d, J=12.9Hz), 3.14(2H, d, J=2.3Hz), 3.80(1H, d, J=13.5Hz), 4.02 (1H, dd, J=3.0, 13.5Hz) | |
| 6 | 0.77(3H, s), 0.84(3H, s), 0.89(3H, s), 1.1~1.4(6H, m), 1.5~1.8(12H, m), 2.18(1H, d, J=10.2Hz), 2.24(1H, d, J=10.6Hz), 2.36(2H, dd, J=6.9, 7.6Hz), 2.48(2H, s) | (FAB) 264 (MH$^+$) |
| 7 | 0.77(3H, s), 0.84(3H, s), 0.89(3H, s), 1.1~1.8(18H, m), 2.17(1H, d, J=10.6 Hz), 2.25(1H, d, J=10.6Hz), 2.35(2H, t, J=7.6Hz), 2.48(2H, d, J=2.6Hz) | (FAB) 278 (MH$^+$) |
| 8 | 0.78(3H, s), 0.85(3H, s), 0.90(3H, s), 1.2~1.8(22H, m), 2.21(1H, d, J=10.6 Hz), 2.27(1H, d, J=10.6Hz), 2.78(2H, dd, J=7.3, 7.9Hz), 2.50(1H, s), 2.51 (1H, s) | (FAB) 292 (MH$^+$) |
| 9 | 0.77(3H, s), 0.85(3H, s), 0.90(3H, s), 1.0~1.8(22H, m), 2.20(1H, d, J=10.2 Hz), 2.25(1H, d, J=10.6 Hz), 2.34(2H, t, J=7.3Hz), 2.49(2H, s) | (FAB) 292 (MH$^+$) |
| 10 | 0.77(3H, s), 0.85(3H, s), 0.90(3H, s), 1.0~1.9(20H, m), 2.20(1H, d, J=10.2 Hz), 2.27(1H, d, J=10.6 Hz), 2.32 (2H, t, J=7.3Hz), 2.49(2H, s), 2.50(1H, s) | (FAB) 278 (MH$^+$) |
| 11 | 0.76(3H, s), 0.84(3H, s), 0.89(3H, s) 1.0~1.9(16H, m), 2.10(2H, d, J=7.3 Hz), 2.1~2.2(1H, m), 2.19(1H, t, J=10.6Hz), 2.40(1H, dd, J=3.6, 10.6Hz), 2.46(1H, d, J=10.6Hz) | (FAB) 250 (MH$^+$) |
| 12 | 0.76(3H, s), 0.84(3H, s), 0.89(3H, s), 1.1~1.3(3H, m), 1.4~1.8(13H, m), 2.10(2H, d, J=7.6 Hz), 2.1~2.2(1H, m), 2.23(1H, d, J=10.6 Hz), 2.40(1H, dd, J=3.3, 10.6Hz), 2.47(1H, d, J=10.6 Hz) | (FAB) 250 (MH$^+$) |
| 13 | 0.81(3H, s), 0.87(3H, s), 0.92(3H, s), 1.0~2.0(15H, m), 2.2~2.9(5H, m) | (FAB) 236 (MH$^+$) |
| 14 | 0.77(3H, a), 0.84(3H, s), 0.89(3H, a) 1.2~2.1(22H, m), 2.23(2H, s), 2.36 (2H, dd, J=7.6, 8.6Hz), 2.47(1H, d, J=10.9Hz), 2.53(1H, d, 10.9Hz) | (FAB) 316 (MH$^+$) |
| 15 | 0.77(3H, s), 0.85(3H, s), 0.90(3H, s), 1.4~1.9(22H, m), 2.18(1H, d, J=10.6 Hz), 2.26(1H, d, J=10.6Hz), 2.34(2H, t, J=7.6Hz), 2.48(1H, s), 2.49(1H, s) | (FAB) 316 (MH$^+$) |
| 16 | 0.78(3H, s), 0.85(3H, s), 0.90(3H, s), 1.5~1.9(22H, m), 2.1~2.3(2H, m), 2.36(2H, t, J=7.3Hz), 2.52(2H, s) | (FAB) 316 (MH$^+$) |
| 18 | 0.70(3H, s), 0.78(3H, s), 0.82(3H, s), 0.8~0.9(3H, m), 1.1~1.8(17H, m), 2.1~2.2(2H, m), 2.3~2.4(2H, m), 2.4 ~2.5(2H, m) | (FAB) 278 (MH$^+$) |
| 19 | 0.70 (3H, s), 0.71(3H, s), 0.78(3H, s), 0.83(3H, s), 1.1~2.0(21H, m), 2.1~ 2.6(6H, m) | (FAB) 330 (MH$^+$) |
| 20 | 0.75(3H, s), 0.83(3H, s), 0.92(3H, s), 1.5~1.8(18H, m), 2.16(2H, s), 2.42 (2H, s), 2.48(1H, dd, J=3.6, 10.6Hz), 2.64(1H, d, J=10.2Hz) | (FAB) 288 (MH$^+$) |
| 21 | 0.79(3H, s), 0.86(3H, s), 0.92(3H, s), 1.4~1.9(22H, m), 2.2~2.6(6H, m) | (FAB) 304 (MH$^+$) |
| 22 | 0.73(3H, s), 0.82(3H, s), 0.92(3H, s), 1.4~1.8(20H, m), 1.92(2H, s), 2.10 (1H, d, J=10.2Hz), 2.41(1H, dd, J=10.2, 10.6Hz), 2.48(1H, d, J=10.2Hz), 2.72 (1H, d, J=10.2Hz) | (FAB) 302 (MH$^+$) |
| 23 | 0.79(3H, s), 0.86(3H, s), 0.91(3H, s) 1.3~2.2(21H, m), 2.2~2.3(2H, m), 2.3~2.4(2H, m), 2.5~2.6(2H, m) | (EI) 331 (MH$^+$) |
| 24 | 0.79(3H, s), 0.86(3H, s), 0.91(3H, s) 1.3~2.2(21H, m), 2.2~2.3(2H, m), 2.3~2.4(2H, m), 2.5~2.6(2H, m), 3.23(1.5H, s), 3.24(1.5H, s) | (FAB) 346 (MH$^+$) |
| 25 | 0.78(3H, s), 0.85(3H, s), 0.90(3H, s), 1.4~2.2(21H, m), 2.2~2.3(2H, m), 2.36(2H, t, J=7.3Hz), 2.51(2H, s0 | (FAB) 350 (MH$^+$) |
| 26 | 0.79(1.5H, s), 0.80(1.5H, s), 0.86 (1.5H, s), 0.87(1.5H, s) 0.91(1.5H, s), 0.93(1.5H, s), 1.5~2.1(21H, m), 2.3~ 2.4(2H, m), 2.4~2.5(2H, m), 2.6~2.7 | (FAB) 392 (MH$^+$) |

TABLE 6-continued

| Exam. No. | $^1$H-NMR (CDCl$_3$) δ (ppm) | MS |
|---|---|---|
|  | (2H, m), 7.1~7.4(5H, m) |  |
| 27 | 0.81(3H, s), 0.87(3H, s), 0.94(3H, s) 1.4~2.0(20H, m), 2.2~2.3(2H, m) 2.4 ~2.5(2H, m), 2.5~2.6(2H, m), 3.8~ 3.9(1H, m) | (FAB) 332 (MH$^+$) |
| 28 | 0.78(1.5H, s), 0.79(1.5H, s), 0.85(3H, s), 0.90(1.5H, s), 0.92(1.5H, s), 1.5~ 2.0(20H, m), 2.2~2.3(2H, m), 2.4~ 2.5(2H, m), 2.5~2.6(2H, m), 2.98 (0.5H, bs), 3.12(0.5H, bs), 7.1~7.5 (5H, m) | (FAB) 392 (MH$^+$) |
| 29 | 0.78(1.5H, s), 0.79(1.5H, s), 0.85 (1.5H, s), 0.91(1.5H, s), 0.92(1.5H, s), 1.5~2.0(20H, m), 2.2~2.3(2H, m), 2.4~2.6(4H, m), 2.98(0.5H, bs), 3.12(0.5H, bs), 7.1~7.5(5H, m) | (FAB) 392 (MH$^+$) |
| 30 | 0.79(3H, s), 0.86(3H, s), 0.91(3H, s), 1.3~2.2(21H, m), 2.2~2.3(2H, m), 2.3~2.4(2H, m), 2.5~2.6(2H, m)3.23 (1.5H, s), 3.24(1.5H, s) | (FAB) 346 (MH$^+$) |
| 31 | 0.79(3H, s), 0.86(3H, s), 0.91(3H, s), 1.3~2.2(21H, m), 2.2~2.3(2H, m), 2.3~2.4(2H, m), 2.5~2.6(2H, m) | (FAB) 332 (MH$^+$) |
| 32 | 0.78(3H, s), 0.85(3H, s), 0.90(3H, s), 1.4~2.2(21H, m), 2.2~2/3(2H, m), 2.3~2.4(2H, m), 2.51(2H, s) | (FAB) 350 (MH$^+$) |
| 33 | 0.79(1.5H, s), 0.80(1.5H, s), 0.86 (1.5H, s), 0.87(1.5H, s), 0.91(1.5H, s), 0.93(1.5H, s), 1.5~2.1(21H, m), 2.3~2.4(2H, m), 2.4~2.5(2H, m), 2.6 ~2.7(2H, m), 7.1~7.4(5H, m) | (FAB) 392 (MH$^+$) |
| 34 | 0.81(3H, s), 0.87(3H, s), 0.94(3H, s), 1.4~2.0(20H, m), 2.2~2.3(2H, m), 2.4~2.5(2H, m), 2.5~2.6(2H, m), 3.8 ~3.9(1H, m) | (FAB) 332 (MH$^+$) |
| 35 | 0.70(3H, s), 0.71(3H, s), 0.78(3H, s), 0.83(3H, s), 1.1~2.0(21H, m), 2.1~ 2.6(6H, m) | (FAB) 330 (MH$^+$) |
| 36 | 0.78(3H, s), 0.85(3H, s), 0.91(3H, s), 1.1~2.0(24H, m), 2.1~2.2(2H, m), 2.2~2.3(2H, m), 2.4~2.5(2H, m) | (FAB) 330 (MH$^+$) |
| 37 | 0.78(3H, s), 0.86(3H, s), 0.91(3H, s), 1.2~2.1(24H, m), 2.1 2.2(2H, m), 2.2 ~2.3(2H, m), 2.4~2.5(2H, m) | (FAB) 330 (MH$^+$) |
| 38 | 0.76(3H, s), 0.83(3H, s), 0.91(3H, s), 1.5~2.0(21H, m), 2.1~2.2(2H, m), 2.2~2.3(2H, m), 2.4~2.5(2H, m) | (FAB) 302 (MH$^+$) |
| 39 | 0.74(3H, s), 0.83(3H, s), 0.91(3H, s,) 1.5~1.8(20H, m), 1.90(2H, s), 2.1~ 2.5(4H, m) | (FAB) 302 (MH$^+$) |
| 40 | 0.74(3H, s), 0.83(3H, s), 0.90(3H, s) 1.5~1.8(20H, m), 1.90(2H, s), 2.1~ 2.5(4H, m) | (FAB) 302 |

Data of the products in Examples 23–26 and 30–33 are that of a mixture of stereoisomer (mixture of 1:1, measured by gas chromatography). Data of the products in Examples 27–29 and 34 are a mixture of stereoisomer.

TABLE 7

| Exam. No. | $^1$H-NMR (CDCl$_3$) δ (ppm) | MS |
|---|---|---|
| 43 | 0.72(1.5H, s, CH$_3$), 0.86(3H, s, CH$_3$), 0.88(1.5H, s, CH$_3$), 0.97(1.5, s, CH$_3$), 0.98(1.5H, s, CH$_3$), 1.1~1.9(5H, m, CH$_2$x2, CH), 2.92(1H, d, CH$_2$, J=13.5Hz), 3.32(1H, dd, CH$_2$, J=2.6, 11.9Hz), 3.46 (1H, d, CH$_2$, J=11.9Hz), 3.89(1H, d, CH$_2$, J=13.2Hz), 4.10(1H, d, CH$_2$, J=13.2Hz), 4.18(1H, d, CH$_2$, J=12.5Hz), 7.34(1H, d, Ar-H, J=6.9Hz), 7.43(1H, dd, Ar-H, J=7.3, 7.9Hz), 7.4~7.6(2H, m, Ar-H), |  |

TABLE 7-continued

| Exam. No. | $^1$H-NMR (CDCl$_3$) δ (ppm) | MS |
|---|---|---|
|  | 7.77(1H, d, Ar-H, J=7.9Hz), 7.87(1H, d, Ar-H, J=7.3Hz), 7.97(1H, d, Ar-H, J=7.6Hz) |  |
| 44 | 0.75(1.5H, s, CH$_3$), 0.83(3H, s, CH$_3$), 0.86(1.5H, s, CH$_3$), 0.94(1.5, s, CH$_3$), 0.95(1.5H, s, CH$_3$), 1.3~1.8(5H, m, CH$_2$x2, CH), 2.87(1H, d, CH$_2$, J=13.5Hz), 3.14(1H, dd, CH$_2$, J=13.5, 11.9Hz), 3.86 (1H, d, CH$_2$, J=13.5Hz), 3.88(2H, s, CH$_2$, J=2.6, 13.5Hz), 4.08(1H, dd, CH$_2$, J=2.6, 13.5Hz), 7.3~ 7.5(3H, m, Ar-H), 7.68(1H, s, Ar-H), 7.8~7.9(3H, m. Ar-H) |  |
| 45 | 0.81(3H, s. CH$_3$), 0.88(3H, s. CH$_3$), 0.94 (3H, s, CH$_3$), 1.5~1.8(5H, m. CH$_2$x2, CH), 2.33(1H, d, CH$_2$, J=10.2Hz), 2.45(1H, d, CH$_2$, J=10.2Hz), 2.6~2.8(4H, m, CH$_2$x2), 3.23(2H, dd, CH$_2$, J=7.6, 8.3Hz), 7.39(2H, d, Ar-H, J=5.6Hz), 7.5~7.6 (2H, m. Ar-H), 7.6~7.7(1H, m, Ar-H), 7.85(1H, d, Ar-H, J=7.6Hz), 8.08(1H, d, Ar-H, J=7.6Hz) | (FAB) 308 (MH$^+$) |
| 46 | 0.80(3H, s. CH$_3$), 0.86(3H, s. CH$_3$). 0.93 (3H, s, CH$_3$), 1.5~1.8(5H, m. CH$_2$x2, CH), 2.30(1H, d, CH$_2$, J=9.9Hz), 2.41(1H, d, CH$_2$, J=10.9Hz), 2.6~2.8(4H, m, CH$_2$x2), 2.93(2H, dd, CH$_2$, J=7.6Hz), 7.3~7.5 (3H, m, Ar-H), 7.68(1H, s, Ar-H), 7.7~ 7.9(3H, m. Ar-H) | (FAB) 308 (MH$^+$) |
| 47 | 0.77(3H, s, CH$_3$), 0.84(3H, s. CH$_3$), 0.91 (3H, s, CH$_3$) 1.4~1.8(5H, m. CH$_2$x2, CH), 2.24(1H, d, CH$_2$, J=10.2Hz), 2.40(1H, d, CH$_2$, J=10.9Hz), 2.5~2.7(2H, m, CH$_2$), 2.78(2H, t, CH$_2$, J=7.9Hz), 2.95 (2H, t, CH$_2$, J=7.3Hz), 7.10(1H, dd, pyridine, J=6.3, 7.6Hz), 7.2~7.3(1H, m. pyridine), 7.58(1H, dt, pyridine, J=2.0, 7.6Hz), 8.51(1H, d, pyridine, J=4.0Hz) | (FAB) 259 (MH$^+$) |
| 48 | 0.78(3H, s, CH$_3$), 0.85(3H, s, CH$_3$), 0.91 (3H, s, CH$_3$), 1.4~1.7(5H, m, CH$_2$x2, CH), 2.21(1H, d, CH$_2$, J=10.6Hz), 2.36 (1H, d, CH$_2$, J=10.2Hz), 2.5~2.8(6H, m, CH$_2$x3), 7.16(2H, d. pyridine, J=5.9 Hz), 8.48(2H, d, pyridine, J=5.9Hz) | (FAB) 259 (MH$^+$) |
| 49 | 0.81(3H, s, CH$_3$), 0.88(3H, s, CH$_3$), 0.94 (3H, s, CH$_3$), 1.5~1.8(5H, m, CH$_2$x2, CH), 2.33(1H, d, 10.2Hz, CH$_2$) 2.45(1H, d, J=10.6Hz, CH$_2$) 2.62(1H, dd, J=10.2, 10.6Hz, CH$_2$) 2.76(2H, dd, J=7.6, 8.3 Hz, CH$_2$), 2.78(1H, d, J=10.6Hz, CH$_2$), 3.24(2H, dd, J=7.6, 8.3Hz, CH$_2$), 7.4~ 7.6(4H, m, Ar-H), 7.71(1H, dd, J=4.0, 5.6Hz, Ar-H), 7.85(1H, d, J=7.6Hz, Ar-H), 8.08(1H, d, J=8.6Hz, Ar-H) | (FAB) 308 (MH$^+$) |
| 50 | 0.80(3H, s, CH$_3$), 0.86(3H, s, CH$_3$), 0.93 (3H, s, CH$_3$), 1.5~1.9(5H, m, CH$_2$x2, CH), 2.30(1H, d, J=10.6Hz, CH$_2$), 2.40 (1H, d, J=10.6Hz, CH$_2$), 2.6~2.8(4H, m, CH$_2$x2), 2.93(2H, dd, J=6.9, 8.3Hz, CH$_2$), 7.3~7.5(3H, m. Ar-H), 7.68(1H, s, Ar-H), 7.7~7.9(3H, m, Ar-H) | (FAB) 308 (MH$^+$) |
| 51 | 0.78(3H, s, CH$_3$), 0.85(3H, s, CH$_3$), 0.91 (3H, s, CH$_3$), 1.4~1.8(5H, m, CH$_2$x2, CH), 2.2~2.3(1H, m, CH$_2$), 2.41(1H, d, J=10.2Hz, CH$_2$), 2.5~3.0(6H, m. CH$_2$x3), 7.10(1H, dd, J=4.3, 7.6Hz, pyridine), 7.23(1H, d, J=8.2Hz, pyridine), 7.58 (1H, dt, J=1.3, 7.6Hz, pyridine), 8.51 (1H, d, J=5.0Hz, pyridine) | (FAB) 259 (MH$^+$) |
| 52 | 0.78(3H, s, CH$_3$), 0.85(3H, s, CH$_3$), 0.91 (3H, s, CH$_3$), 1.5~1.8(5H, m, CH$_2$x2, CH), 2.22(1H, d, J=10.2Hz, CH$_2$), 2.36 (1H, d, J=10.6Hz, CH$_2$), 2.5~2.8(6H, m. CH$_2$x3), 7.20(1H, dd, J=7.6, 7.9Hz, pyridine), 7.57(1H, d, J=7.9, Hz, pyridine), 8.43(1H, d, J=3.6Hz, pyridine), 8.48(1H, d, J=2.0Hz, | (FAB) 301 (MH$^+$) |

TABLE 7-continued

| Exam. No. | ¹H-NMR (CDCl₃) δ (ppm) | MS |
|---|---|---|
| 53 | pyridine) 0.78(3H, s, CH₃), 0.85(3H, s, CH₃), 0.91 (3H, s, CH₃), 1.5~1.8(5H, m, CH₂x2, CH), 2.21(1H, d, J=10.2Hz, CH₂), 2.36 (1H, d, J=10.6Hz, CH₂), 2.50(1H, dd. J=10.2, 10.6Hz, CH₂), 2.60(1H, d, J=10.6Hz, CH₂), 2.65(2H, t, J=6.6, Hz, CH₂), 2.75(2H, t, J=6.6Hz, CH₂), 7.17 (2H, d, J=5.6Hz, pyridine), 8.47(2H, d, J=5.9Hz, pyridine | (FAB) 259 (MH⁺) |
| 54 | 0.79(3H, s, CH₃), 0.86(3H, s, CH₃), 0.91 (3H, s, CH₃), 1.4~1.8(5H, m, CH₂x2, CH), 2.25(1H, d, J=10.2Hz, CH₃), 2.35 (1H, d, J=10.2Hz, CH₂), 2.5~2.8(4H, m, CH₂x2), 5.91(2H, s, CH₂), 6.7~6.8 (3H, m, Ar-H) | (FAB) 301 (MH⁺) |
| 55 | 0.79(3H, s, CH₃), 0.86(3H, s, CH₃), 0.92 (3H, s, CH₃), 1.5~1.8(5H, m, CH₂x2, CH), 2.27(1H, d, J=10.6Hz, CH₃), 2.36 (1H, d, J=10.6Hz, CH₂), 2.66(2H, dd, J=6.9, 7.3Hz, CH₂), 2.97(2H, dd, J=6.9, 7.3Hz, CH₂), 6.83(1H, d, J=3.3Hz, thiophene), 6.91(1H, dd, J=3.3, 5.3Hz thiophene), 7.12(1H, d, J=5.3Hz, thiophene) | (FAB) 264 (MH⁺) |

TABLE 8

| Compound No. | ¹H-NMR (CDCl₃) δ (p m) | MS |
|---|---|---|
| 58α | 0.80(3H, s), 0.87(3H, s), 0.92(3H, s), 1.5 ~1.9(18H, m), 1.94(2H, bs), 2.13(1H, bs), 2.36(2H, s), 2.4~2.5(2H, m), 2.6~2.7 (2H, m) | (FAB) 332 (MH⁺) |
| 58β | 0.79(3H, s), 0.85(3H, s), 0.91(3H, s), 1.35(2H, d, J=12.5Hz.), 1.5~1.8(16H, m), 1.89(2H, bs), 2.07(1H, bs), 2.30(2H, s), 2.4~2.5(2H, .m), 2.5~2.6(2H, m) | (FAB) 332 (MH⁺) |
| 59α | 0.80(3H, s), 0.87(3H, s), 0.92(3H, s), 1.5 ~1.9(18H, m), 1.94(2H, bs), 2.13(1H, bs), 2.36(2H, s), 2.4~2.5(2H, m), 2.6~2.7 (2H, m) | (FAB) 332 (MH⁺) |
| 59β | 0.79(3H, s), 0.85(3H, s), 0.91(3H, s), 1.35(2H, d, J=12.5Hz), 1.5~1.8(16H, m), 1.89(2H, bs), 2.07(1H, bs), 2.30(2H, s), 2.4~2.5(2H, m), 2.5~2.6(2H, m) | (FAB) 346 (MH⁺) |
| 60β | 0.87(3H, s), 0.92(3H, s), 0.99(3H, s), 1.3 ~1.5(2H, m), 1.6~2.0(17H, m), 2.0~2.3 (2H, m), 2.5~2.6(1H, m), 2.7~2.9(4H, m), 3.1~3.2(1H, m), 3.23(3H, s) | (FAB) 346 (MH⁺) |
| 63 | 0.81(3H, s), 0.88(3H, s), 0.93(3H, s), 1.4~2.2(21H, m), 2.2~2.7(6H, m) | (FAB) 350 (MH⁺) |
| 63β | 0.79(3H, s), 0.85(3H, s), 0.91(3H, s), 1.5 ~2.1(21H, m), 2.3~2.4(2H, m), 2.4~2.5 (2H, m), 2.5~2.6(2H, m), 7.1~7.4(5H, m) | (FAB) 392 (MH⁺) |

What is claimed is:

1. An azepine compound of the formula

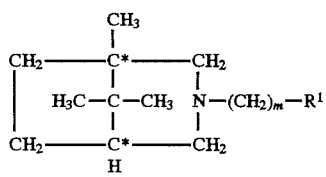

(1)

wherein
R is (a)

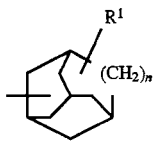

(2)

in which R¹ is hydrogen, lower alkyl, lower alkoxy, hydroxy, halogen, or optionally substituted phenyl, and n is 0 or 1, (b) cycloalkyl of $C_{5-8}$ which is optionally substituted by lower alkyl, (c) norbornyl, (d) bicyclo [3.3.1]nonyl, (e) naphthyl, (f) 1,3-benzodioxolyl, (g) pyridyl, or (h) thienyl, m is an integer of 0–4, and C* is an asymmetric carbon, and nontoxic salts thereof.

2. The compound of claim 1, selected from the group consisting of (1S)-3-[2-(1-adamantyl)ethyl]-1,8,8-trimethyl-3-azabicyclo[3.2.1]octane, (1S)-3-[2-(2-norbornyl)ethyl]-1, 8,8-trimethyl-3-azabicyclo[3.2.1]octane, (1S)-3-(2-cyclopentylethyl)-1,8,8-trimethyl-3-azabicyclo[3.2.1] octane, (1S)-3-(2-cyclohexylethyl)-1,8,8-trimethyl-3-azabicyclo[3.2.1]octane, and (1R)-3-cyclohexylacetyl-1,8, 8-trimethyl-3-azabicyclo[3.2.1]octane.

3. The compound of claim 1, selected from the group consisting of (1R)-3-(2-cyclohexylethyl)-1,8,8-trimethyl-3-azabicyclo[3.2.1]octane, (1S)-3-(2-cycloheptylethyl)-1,8,8-trimethyl-3-azabicyclo[3.2.1]octane, (1S)-3-(2-cyclooctylethyl)-1,8,8-trimethyl-3-azabicyclo[3.2.1]octane, (1S)-3-(4-cyclohexyl-1-butyl)-1,8,8-trimethyl-3-azabicyclo [3.2.1]octane, and (1S)-3-(3-cyclohexylpropyl)-1,8,8-trimethyl-3-azabicyclo[3-2-1]octane.

4. The compound of claim 1, selected from the group consisting of (1S)-3-cyclohexylmethyl-1,8,8-trimethyl-3-azabicyclo[3.2.1]octane, (1R)-3-cyclohexylmethyl-1,8,8-trimethyl-3-azabicyclo[3.2.1]octane, (1S)-3-cyclohexyl-1,8, 8-trimethyl-3-azabicyclo[3.2.1]octane, (1R)-3-[2-(1-adamantyl)ethyl]-1,8,8-trimethyl-3-azabicyclo[3.2.1] octane, and (1S)-3-[2-(2-adamantyl)ethyl]-1,8,8-trimethyl-3-azabicyclo[3.2.1]octane.

5. The compound of claim 1, selected from the group consisting of (1R)-3-[2-(2-adamantyl)ethyl]-1,8,8-trimethyl-3-azabicyclo[3.2.1]octane, (1S)-3-[2-(2-adamantyl)ethyl]-1,8,8-trimethyl-3-azabicyclo[3.2.1] octane, (1S)-3-[2-(4-methylcyclohexyl)ethyl]-1,8,8-trimethyl-3-azabicyclo[3.2.1]octane, (1S)-3-[2-(3-methyl-1-adamantyl)ethyl]-1,8,8-trimethyl-3-azabicyclo[3.2.1] octane, and (1S)-3-(3-noradamantylmethyl)-1,8,8-trimethyl-3-azabicyclo[3.2.1]octane.

6. The compound of claim 1, selected from the group consisting of (1S)-3-[2-(bicyclo[3.3.1]nonan-9-yl)-ethyl]-1, 8,8-trimethyl-3-azabicyclo[3.2.1]octane, (1S)-3-(1-adamantylmethyl)-1,8,8-trimethyl-3-azabicyclo[3.2.1] octane, (1S)-3-[2-(5-hydroxy-2-adamantyl)ethyl]-1,8,8-trimethyl-3-azabicyclo[3.2.1]octane, (1S)-3-[2-(5-methoxy-2-adamantyl)ethyl]-1,8,8-trimethyl-3-azabicyclo[3.2.1] octane, and (1S)-3-[2-(5-chloro-2-adamantyl)ethyl]-1,8,8-trimethyl-3-azabicyclo[3.2.1]octane.

7. The compound of claim 1, selected from the group consisting of (1S)-3-[2-(5-phenyl-2-adamantyl)ethyl]-1,8,8-trimethyl- 3-azabicyclo[3.2.1]octane, (1S)-3-[2-(4-hydroxy-2-adamantyl)ethyl]-1,8,8-trimethyl-3-azabicyclo[3.2.1] octane, (1S)-3-[2-(4-phenyl-2-adamantyl)ethyl]-1,8,8-trimethyl-3-azabicyclo[3.2.1]octane, (1R)-3-[2-(4-phenyl-2-adamantyl)ethyl]-1,8,8-trimethyl-3-azabicyclo[3.2.1]

octane, and (1R)-3-[2-(5-methoxy-2-adamantyl)ethyl]-1,8,8-trimethyl-3-azabicyclo[3.2.1]octane.

8. The compound of claim 1, selected from the group consisting of (1R)-3-[2-(5-hydroxy-2-adamantyl)ethyl]-1,8,8-trimethyl-3-azabicyclo[3.2.1]octane, (1R)-3-[2-(5-chloro-2-adamantyl)ethyl]-1,8,8-trimethyl-3-azabicyclo[3.2.1]octane, (1R)-3-[2-(5-phenyl-2-adamantyl)ethyl]-1,8,8-trimethyl-3-azabicyclo[3.2-1]octane, (1R)-3-[2-(4-hydroxy-2-adamantyl)ethyl]-1,8,8-trimethyl-3-azabicyclo[3.2.1]octane, (1R)-3-[2-(3-methyl-1-adamantyl)ethyl]-1,8,8-trimethyl-3-azabicyclo[3.2.1]octane, (1S)-3-[3-(2-adamantyl)-1-propyl-1,8,8-trimethyl-3-azabicyclo[3.2.1]octane, (1R)-3-[3-(2-adamantyl)-1-propyl-1,8,8-trimethyl-3-azabicyclo[3.2.1]octane, (1S)-3-[2-(3-noradamantyl)ethyl]-1,8,8-trimethyl-3-azabicyclo[3.2.1]octane, (1S)-3-(2-adamantylmethyl)-1,8,8-trimethyl-3-azabicyclo[3.2.1]octane, and (1R)-3-(2-adamantylmethyl)-1,8,8-trimethyl-3-azabicyclo[3.2.1]octane.

9. The compound of claim 1, selected from the group consisting of (1R)-3-(1-naphthylacetyl)-1,8,8-trimethyl-3-azabicyclo[3.2.1]octane, (1R)-3-(2-naphthylacetyl)-1,8,8-trimethyl-3-azabicyclo[3.2.1]octane, (1R)-3-[2-(1-naphthyl)ethyl]-1,8,8-trimethyl-3-azabicyclo[3.2.1]octane, (1R)-3-[2-(2-naphthyl)ethyl]-1,8,8-trimethyl-3-azabicyclo[3.2.1]octane, (1R)-3-[2-(2-pyridyl)ethyl]-1,8,8-trimethyl-3-azabicyclo[3.2.1]octane, (1R)-3-[2-(4-pyridyl) ethyl]-1,8,8-trimethyl-3-azabicyclo[3.2.1]octane, (1S)-3-[2-(1-naphthyl)ethyl]-1,8,8-trimethyl-3-azabicyclo-[3.2.1]octane, and (1S)-3-[2-(2-naphthyl)ethyl]-1,8,8-trimethyl-3-azabicyclo[3.2.1]octane.

10. The compound of claim 1, selected from the group consisting of (1S)-3-[2-(2-pyridyl)ethyl]-1,8,8-trimethyl-3-azabicyclo[3.2.1]octane, (1S)-3-[2-(3-pyridyl)ethyl]-1,8,8-trimethyl-3-azabicyclo[3.2.1]octane, (1S)-3-[2-(4-pyridyl)ethyl]-1,8,8-trimethyl-3-azabicyclo[3.2.1]octane, (1S)-3-2-(1,3-benzodioxol-5-yl)ethyl]-1,8,8-trimethyl-3-azabicyclo[3.2.1]octane, (1S)-3-[2-(2-thienyl)ethyl]-1,8,8-trimethyl-3-azabicyclo[3.2.1]octane, cis-(1S)-3-[2-(5-hydroxy-2-adamantyl)ethyl]-1,8,8-trimethyl-3-azabicyclo[3.2.1]octane, trans-(1S)-3-[2-(5-hydroxy-2-adamantyl)ethyl]-1,8,8-trimethyl-3-azabicyclo[3.2.1]octane, cis-(1R)-3-[2-(5-hydroxy-2-adamantyl)ethyl]-1,8,8-trimethyl-3-azabicyclo[3.2.1]octane, trans-(1R)-3-[2-(5-hydroxy-2-adamantyl)ethyl]-1,8,8-trimethyl-3-azabicyclo[3.2.1]octane, cis-(1S)-3-[2-(5-methoxy-2-adamantyl)ethyl]-1,8,8-trimethyl-3-azabicyclo[3.2.1]octane, and trans-(1S)-3-[2-(5-methoxy-2-adamantyl)ethyl]-1,8,8-trimethyl-3-azabicyclo[3.2.1]octane.

11. The compound of claim 1, selected from the group consisting of cis-(1R)-3-[2-(5-methoxy-2-adamantyl)ethyl]-1,8,8-trimethyl-3-azabicyclo[3.2.1]octane, trans-(1R)-3-[2-(5-methoxy-2-adamantyl)ethyl]-1,8,8-trimethyl-3-azabicyclo[3.2.1]octane, cis-(1S)-3-[2-(5-chloro-2-adamantyl)ethyl]-1,8,8-trimethyl-3-azabicyclo[3.2.1]octane, trans-(1S)-3-[2-(5-chloro-2-adamantyl)ethyl]-1,8,8-trimethyl-3-azabicyclo[3.2.1]octane, (1R)-3-[2-(5-chloro-2-adamantyl)ethyl]-1,8,8-trimethyl-3-azabicyclo[3.2.1]octane, (1R)-3-[2-(5-chloro-2-adamantyl)ethyl]-1,8,8-trimethyl-3-azabicyclo[3.2.1]octane, cis-(1S)-3-[2-(5-phenyl-2-adamantyl)ethyl]-1,8,8-trimethyl-3-azabicyclo [3.2.1]octane, trans-(1S)-3-[2-(5-phenyl-2-adamantyl)ethyl]-1,8,8-trimethyl-3-azabicyclo[3.2.1]octane, cis-(1R)-3-[2-(5-phenyl-2-adamantyl)ethyl]-1,8,8-trimethyl-3-azabicyclo]3.2.1]octane, and trans-(1R)-3-[2-(5-phenyl-2-adamantyl)ethyl]-1,8,8-trimethyl-3-azabicyclo[3.2.1]octane.

12. A stereoisomeric compound of formula

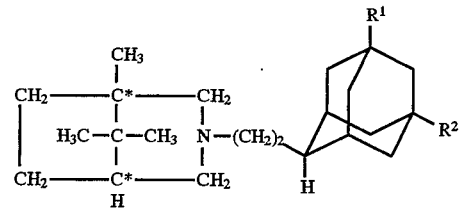

wherein $R^1$ is hydrogen and $R^2$ is hydroxy, lower alkoxy, halogen or phenyl or $R^2$ is hydrogen and $R^1$ is hydroxy, lower alkoxy, halogen or phenyl, and C* is an asymmetric carbon, and nontoxic salts thereof.

13. An azepine derivative of the formula

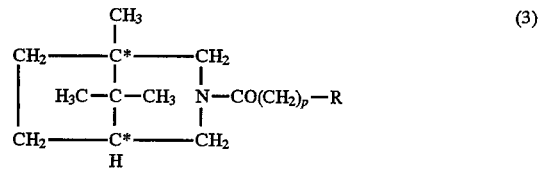
(3)

wherein R is the formula

(2)

in which $R^1$ is hydrogen, lower alkyl, lower alkoxy, hydroxy, halogen, or optionally substituted phenyl, and n is 0 or 1; cycloalkyl of $C_{5-8}$ which is optionally substituted by lower alkyl; norbornyl; bicyclo[3.3.1]nonyl; naphthyl; 1,3-benzodioxolyl; pyridyl; or thienyl, p is an integer of 0–3, and C* is an asymmetric carbon.

14. A pharmaceutical composition for the treatment of σ-receptor related diseases comprising a compound in accordance with claim 1 as an active ingredient and a pharmaceutically acceptable carrier.

15. A pharmaceutical compositions for the treatment of schizophrenia comprising an effective amount of a compound in accordance with claim 1 as an active ingredient and a pharmaceutically acceptable carrier.

16. A pharmaceutical compositions for the treatment of schizophrenia comprising an effective amount of a compound in accordance with claim 12 as an active ingredient and a pharmaceutically acceptable carrier.

17. A pharmaceutical composition comprising a compound in accordance with claim 1 as an active ingredient and a pharmaceutically acceptable carrier.

* * * * *